United States Patent
Eberwine et al.

(10) Patent No.: US 10,583,204 B2
(45) Date of Patent: *Mar. 10, 2020

(54) METHODS FOR TRANSFECTING NUCLEIC ACID INTO LIVE CELLS

(75) Inventors: James Eberwine, Philadelphia, PA (US); Philip G. Haydon, Narberth, PA (US); Jai-Yoon Sul, Bensalem, PA (US); Hajime Takano, Lawrenceville, NJ (US); Chia-Wen Kitty Wu, Philadelphia, PA (US); Fanyi Zeng, Philadelphia, PA (US)

(73) Assignee: THE TRUSTEES OF THE UNIVERSITY OF PENNSYLVANIA, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/426,422

(22) Filed: Mar. 21, 2012

(65) Prior Publication Data

US 2012/0178167 A1 Jul. 12, 2012

Related U.S. Application Data

(63) Continuation of application No. 12/086,471, filed as application No. PCT/US2006/047480 on Dec. 12, 2006.

(60) Provisional application No. 60/749,941, filed on Dec. 13, 2005.

(51) Int. Cl.
*C12N 15/87* (2006.01)
*A61K 48/00* (2006.01)
*C12N 15/10* (2006.01)
*C12N 13/00* (2006.01)

(52) U.S. Cl.
CPC .......... *A61K 48/0083* (2013.01); *C12N 13/00* (2013.01); *C12N 15/1079* (2013.01); *C12N 15/87* (2013.01)

(58) Field of Classification Search
CPC ................ A61K 48/0083; C12N 13/00; C12N 15/1079; C12N 15/87
See application file for complete search history.

(56) References Cited

U.S. PATENT DOCUMENTS

| | | | |
|---|---|---|---|
| 3,711,262 A | 5/1970 | Keck et al. | |
| 5,034,506 A | 7/1991 | Summerton et al. | |
| 5,330,467 A | 7/1994 | Abela | |
| 5,891,634 A | 4/1999 | Petri, Jr. et al. | |
| 6,458,594 B1 | 10/2002 | Baszczynski et al. | |
| 6,753,161 B2 | 6/2004 | Koller et al. | |
| 6,973,245 B2 | 12/2005 | Bocanegra et al. | |
| 2004/0180430 A1* | 9/2004 | West et al. | 435/366 |
| 2004/0235175 A1 | 11/2004 | Gaudernack et al. | |
| 2009/0068742 A1 | 3/2009 | Yamanaka | |
| 2011/0033934 A1* | 2/2011 | Eberwine et al. | 435/455 |
| 2012/0129261 A1* | 5/2012 | Eberwine et al. | 435/455 |
| 2012/0135493 A1* | 5/2012 | Eberwine et al. | 435/173.5 |

FOREIGN PATENT DOCUMENTS

| | | |
|---|---|---|
| EP | 0137504 | 1/1991 |
| EP | 1 083 232 A1 | 9/1999 |
| EP | 1 391 503 A1 | 12/2002 |
| EP | 1270732 | 1/2003 |
| EP | 1225228 | 8/2005 |
| WO | 1996/018741 | 6/1996 |
| WO | 99/14346 | 3/1999 |
| WO | 2001/075164 | 10/2001 |
| WO | 2002/090555 | 11/2002 |
| WO | 03/079883 | 10/2003 |
| WO | 2005/044367 | 5/2005 |
| WO | 2005-168495 | 6/2005 |
| WO | 2006/059084 | 6/2006 |
| WO | 2007/047766 | 4/2007 |
| WO | 2007/084228 | 7/2007 |

OTHER PUBLICATIONS

Dannull et al. Blood, 2005 105: 3206-3213, Prepublished online Dec. 23, 2004.*
Dannull et al. Proceedings of the American Association for Cancer Research Annual Meeting, (Mar. 2004) vol. 45, pp. 495. Meeting Info.: 95th Annual Meeting of the American-Association-for-Cancer-Research. Orlando, FL, USA. Mar. 27-31, 2004 Amer Assoc Canc Res.*
Diaz et al. Society for Neuroscience Abstract Viewer and Itinerary Planner, (2003) vol. 2003, pp. Abstract No. 160.14. Meeting Info.: 33rd Annual Meeting of the Society of Neuroscience. New Orleans, LA, USA. Nov. 8-12, 2003.*
Boczkowski et al. J. Exp. Med. 1996, 184:465-472.*
Nencioni et al., Cancer Gene Therapy (2003) 10, 209-214 (Year: 2003).*
Kalady et al. J. Gastrointest Surg 2004, 8:175-182 (Year: 2004).*
Barrett Lindy E. et al., "Region-directed phototransfection reveals the functional significance of a dendritically synthesized transcription factor," Nature Methods, Jun. 2006, vol. 3, No. 6, pp. 455-460.
Bolstad et al., 2003, "A comparison of normalization methods for high density oligonucleotide array data based on variance and bias" Bioinformatics 19:185-193.
Chen, et al., 2005, "Ventilation-synchronous magnetic resonance microscopy of pulmonary structure and ventilation in mice" Magn. Reson. Med. 53: 69-75.
Dang, et al., 2005, "Comparison of histologic, biochemical, and mechanical properties of murine skin treated with the 1064-nm and 1320-nm Nd:YAG lasers" Exp Dermatol., 14: 876-882.
Eberwine et al., 1992, "Analysis of gene expression in single live neurons," PNAS 89: 3010-3014.

(Continued)

*Primary Examiner* — James D Schultz
(74) *Attorney, Agent, or Firm* — Riverside Law LLP

(57) ABSTRACT

The present invention includes methods for transferring a multigenic phenotype to a cell by transfecting, preferably by phototransfection, and locally transfecting a cell or a cellular process with a laser while the cell is bathed in a fluid medium comprising two or more nucleic acids, thereby introducing the nucleic acid into the interior of the cell. Expression of the nucleic acids results in a multigenic phenotype in the tranfected cell.

14 Claims, 7 Drawing Sheets

(56) References Cited

OTHER PUBLICATIONS

Eberwine, et al., 2001, "Analysis of mRNA populations from single live and fixed cells of the central nervous system". Current protocols in neuroscience (editorial board, Jacqueline N. Crawley et al. ) Chapter 5, Unit 5.3.
Eberwine, 2001, "Single Cell Molecular Biology" Nat Neurosci. 4:1155-1156.
The Gene Ontology Consortium, 2000, "Gene ontology: tool for the unification of biology," Nature Genet. 25:25-29.
Guo et al., 1995, "Laser-mediated gene transfer in rice," Physiologia Plantarym, 93:19-24.
Hanna et al., 2007, "Treatment of sickle cell anemia mouse model with iPS cells generated from autologous skin" Science 318(5858):1920-1923.
Herberholz et al., 2002, "A Lateral Excitatory Network in the Escape Circuit of Crayfish" J Neurosci. 22: 9078-9085.
Huang et al., 2001, "A novel transcription factor inhibitor, SP100030, inhibits cytokine gene expression, but not airway eosinophilia or hyperresponsiveness in sensitized and allergen-exposed rat" Br. J. Pharmacol., 134: 1029-1036.
Huangfu D, et al. (2008) "Induction of pluripotent stem cells from primary human fibroblasts with only Oct4 and Sox2" Nat Biotechnol 26(11):1269-1275.
Izumikawa, et al., 2005, "Auditory hair cell replacement and hearing improvement by Atohl gene therapy in deaf mammals," Nature Medicine, 11(3):271-276.
Kacharmina, et al., 2000, "Stimulation of glutamate receptor protein synthesis and membrane insertion within isolated neuronal dendrites" PNAS, 97:11545-11550.
Kim et al. (2008) "Pluripotent stem cells induced from adult neural stem cells by reprogramming with two factors" Nature 454(7204):646-650.
Maherali et al. (2007) "Directly reprogrammed fibroblasts show global epigenetic remodeling and widespread tissue contribution" Cell Stem Cell 1(1):55-70.
Martinez et al., 2002, "Single-Stranded Antisense siRNAs Guide Target RNA Cleavage in RNAi" Cell 110:563-74.
Mohanty et al., 2003, "Laser-assisted microinjection into targeted animal cells" Biotechnol. Lett. 25: 895-899.
Nakagawa M, et al, 2008, "Generation of induced pluripotent stem cells without Myc from mouse and human fibroblasts" Nat Biotechnol 26(1):101-106.
Needham-VanDevanter, et al., 1984, "Characterization of an adduct between CC-1065 and a defined oligodeoxynucleotide duplex" Nucleic Acids Res., 12:6159-6168.
Neufeld et al., 1985, "Uptake and subcellular distribution of [3H]arachidonic acid in murine fibrosarcoma cells measured by electron microscope autoradiography" J Cell Biol. 101(2):573-581.
Okita et al., 2007, "Generation of germline-competent induced pluripotent stem cells" Nature 448(7151):313-317.
Palumbo, et al., 1996, "Targeted gene transfer in eukaryotic cells by dye-assisted laser optoporation," Journal of Photochemistry and Photobiology, 36(1):41-46.
Paterson, et al., 2005, "Photoporation and cell transfection using a violet diode laser," Optics Express, 13(2):595-600.
Roelandse, et al. 2004, "Hypothermia-Associated Loss of Dendritic Spines" J Neurosci. 24: 7843-7847.
Rowe et al. 2005, "Development of functional neurons from postnatal stem cells in vitro". Stem Cells 23(8):1044-1049.
Schneckenburger, et al., 2002, "Laser-assisted optoporation of single cells" J. Biomed. Opt., 7: 410-416.
Shirahata, et al., 2001, "New technique for gene transfection using laser irradiation" J. Invest. Med., 49: 184-190.
Smits, et al., 2004, "RNA-based gene transfer for adult stem cells and T cells," Leukemia, 18:1898-1902.
Soughayer, et al., 2000, "Characterization of Cellular Optoporation with Distance" Anal. Chem., 72: 1342-1347.
Stadtfeld et al., 2008, "Induced Pluripotent Stem Cells Generated Without Viral Integration" Science 322(5903):945-949.
Stracke et al., 2005, "Optical Nanoinjection of Macromolecules into Vital Cells" J Photochem Photobiol B 81:136-142. (Abstract only).
Takahashi et al., 2006, "Induction of pluripotent stem cells from mouse embryonic and adult fibroblast cultures by defined factors" Cell 126(4):663-676.
Tao, et al., 1987, "Direct gene transfer into human cultured cells facilitated by laser micropuncture of the cell membrane," Proceedings of the National Academy of Science USA, 84:4180-4184.
Tang et al., 2006, "Efficient delivery of small interfering RNA to plant cells by a nanosecond pulsed laser-induced stress wave for posttranscriptional gene silencing," Plant Science 171:375-381.
Tirlapur et al., 2002, "Femtosecond near-infrared laser pulses as a versatile non-invasive tool for intra-tissue nanoprocessing in plants without comprising viability," The Plant Journal: for Cell and Molecular Biology, 31(3): 365-374.
Tirlapur et al., 2002, "Targeted transfection by femtosecond laser," Nature, 418:290-291.
Valles et al., 1997 "Ethanol exposure affects glial fibrillary acidic protein gene expression and transcription during rat brain development" J. Neurochem 69:2484-2493.
Van Driessche, et al., 2005, "Messenger RNA electroporation: an efficient tool in immunotherapy and stem cell research," Folia Histochemica et Cytobiologica, 43(4):213-216.
Van Gelder et al., 1990, "Amplified RNA synthesized from limited quantities of heterogeneous cDNA" PNAS 87 (5): 1663-1667.
Wernig et al., 2008, "Neurons derived from reprogrammed fibroblasts functionally integrate into the fetal brain and improve symptoms of rats with Parkinson's disease" PNAS 105(15):5856-5861.
Zeira, et al., "Femtosecond Infrared Laser—An Efficient and Safe In Vitro Gene Delivery System for Prolonged Expression," Molecular Therapy, 8(2):342-350.
Boczkowski et al., "Induction of Tumor Immunity and Cytotoxic T Lymphocyte Responses Using Dendritic Cells Transfected with Messenger RNA Amplified from Tumor Cells1", *Cancer Research*, 60: 1028-1034, Feb. 15, 2000.
Elango et al., "Optimized Transfection of mRNA Transcribed from a d (A/T) 100 Tail-Containing Vector", *Biochemical and Biophysical Research Communications*, 330: 958-966, 2005.
Fisher et al., "The Transmembrane Domain of Diphtheria Toxin Improves Molecular Conjugate Gene Transfer", *Biochemical Journal*, 321: 49-58, Jan. 1, 1997.
Kalady et al., "Sequential Delivery of Maturation Stimuli Increases Human Dendritic Cell IL-12 Production and Enhances Tumor Antigen-Specific Immunogenicity", *Journal of Surgical Research*, 116: 24-31, 2004.
Kim et al., "Transcriptome Transfer Provides a Model for Understanding the Phenotype of Cardiomyocytes", *PNAS Early Edition*, 2011, retrieved online: www.pnas.org/cgi/doi/10.1073/pnas.1101223108.
Malone et al., "Cationic Liposome-Mediated RNA Transfection", *Proceedings of the National Academy of Science*, 86: 6077-6081, Aug. 1989.
Nair et al., "Induction of Primary Carcinoembryonic Antigen (CEA)—Specific Cytotoxic T Lymphocytes in Vitro Using Human Dendritic Cells Transfected with RNA", *Nature Biotechnology*, 16: 364-369, Apr. 1998.
Petrova et al., "Lymphatic Endothelial Reprogramming of Vascular Endothelial Cells by the Prox-1 Homeobox Transcription Factor", *The EMBO Journal*, 21(17): 4593-4599, 2002.
Rakhmilevich et al, "Eradication of Established Metastatic Murine Tumors Following Particle-Mediated Delivery of IL-[1]12 Gene into the Skin", *Proceedings of the American Association for Cancer Research Annual*, 37: 347, Apr. 20-24, 1996.
Sawai Keisuke et al., "A Novel Method of Cell-Specific mRNA Transfection", *Molecular Genetics and Metabolism*, 64: 44-51, Jan. 7, 1998.
U.S. Appl. No. 60/726,915, filed Oct. 14, 2005, Hu.

(56) References Cited

OTHER PUBLICATIONS

Rakhmilevich et al., 2000, Gene Therapy of Cancer: Methods in Molecular Medicine, Ed, W. Walther and U. Stein, Humana Press, Inc. Totowa NJ, vol. 30: 331-344.

* cited by examiner

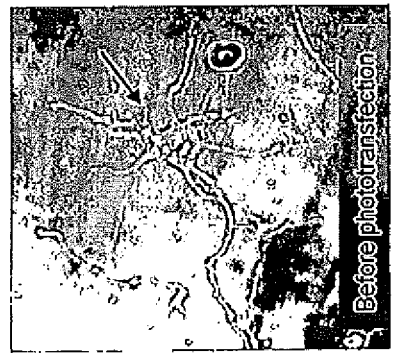
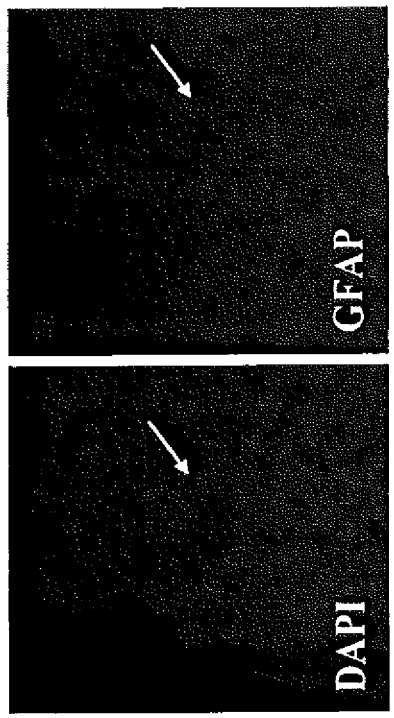
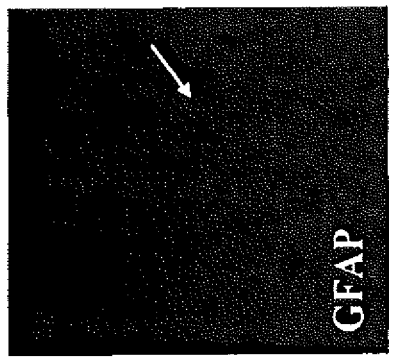

METHODS FOR TRANSFECTING NUCLEIC ACID INTO LIVE CELLS

CROSS-REFERENCE TO RELATED APPLICATIONS

This application is a continuation of and claims priority to U.S. application Ser. No. 12/086,471, filed Jan. 31, 2012, which claims priority to International Application No. PCT/US06/047480, filed Dec. 12, 2006, and published under PCT Article 21(2) in English, which claims priority under 35 U.S.C. § 119(e) to U.S. Provisional Application No. 60/749,941, filed Dec. 13, 2005, all of which applications are incorporated by reference herein in their entireties.

BACKGROUND OF THE INVENTION

A serious shortcoming of current gene therapy strategies and conventional methods of introducing macromolecules, particularly nucleic acids, into cells is the inability of vector and delivery system combinations to deliver nucleic acids efficiently into the interior of cells of a targeted population. Methods for introducing macromolecules, particularly nucleic acid, into a single cell or group of cells are varied. Methods commonly used include chemical treatments, liposome mediated transfection, microinjection, electroporation and particle bombardment. However, these techniques can be time-consuming and suffer from low yields or poor cell survival, and not all cell types are amenable to these methods of introducing macromolecules into a cell.

Many compositions and methods are known for delivering a nucleic acid to an animal cell or tissue. Such compositions include "naked" (i.e. non-complexed) nucleic acids, nucleic acids complexed with cationic molecules such as polylysine or liposome-forming lipids, and virus vectors. Naked nucleic acids can be taken up by various animal cells, but are subject to nucleolysis, both inside and outside of cells that take them up. Nucleic acid analogs which are relatively resistant to nucleolysis, including phosphorothioate nucleic acid analogs, are used to overcome nucleolysis. However, when incorporation of the nucleic acid into the genome of the target cell is desired, the use of nucleic acid analogs are of limited use.

Numerous vectors comprising a nucleic acid complexed with a compound to improve stability or uptake of the nucleic acid by a target cell have also been described. Such compounds include, for example, calcium phosphate, polycations such as diethylaminoethyl-dextran, polylysine, or polybrene, and liposome-forming lipids such as didocylmethylammonium bromide and Lipofectamine®. However, traditional transfections with a DNA vector complexed with another composition severely limit the ability to control the amount of mRNA transcription or protein expression, resulting in unnatural levels of protein expression which cannot otherwise be controlled.

Virus vectors are generally regarded as the most efficient nucleic acid vectors. Recombinant replication-defective virus vectors are often used to transduce (i.e., infect) animal cells. Such vectors have included retrovirus, adenovirus, adeno-associated virus vectors, and herpesvirus vectors. While highly efficient for gene transfer, a major disadvantage associated with the use of virus vectors is the inability of many virus vectors to infect non-dividing cells, limiting the cell types that can be transfected. Further, if integration of a nucleic acid into the genome is not desired, certain viruses, such as retrovirus vectors, are not recommended. Further, there is often a size limit to the length of the gene or cDNA that can be introducted into a vector. In addition, virus gene vectors do not permit appropriate regulation of gene expression over time in transfected cells.

Despite the development and refinement of the techniques discussed above, there remains a need in the art for methods and compositions which can be used to enhance the delivery of a nucleic acid to a desired cell which is to be transfected with the nucleic acid. Further, the techniques discussed above are limited to delivering one or only a few nucleic acids to study the expression of these limited numbers of nucleic acids on a cellular phenotype. The present invention provides novel method for delivering nucleic acids to a cell, and for determining the effect of multigenic nucleic acid expression on a cell.

BRIEF SUMMARY OF THE INVENTION

The present invention encompasses a method of transferring a multigenic phenotype to a cell, the method comprising irradiating a cell with a laser, wherein the cell is bathed in a fluid medium comprising two or more isolated nucleic acids, wherein the laser porates a cellular membrane of the cell and the nucleic acids enter the cell, and wherein the nucleic acids are expressed by the cell, thereby transferring a multigenic phenotype to a cell.

In one embodiment, the cell is selected from the group consisting of a eukaryotic cell and a prokaryotic cell.

In another embodiment, the eukaryotic cell is a non-mammalian cell.

In yet another embodiment, the cell is a plant cell.

In still another embodiment, the cell is a protozoan.

In one embodiment, the nucleic acids are isolated from a cell.

In another embodiment, the isolated nucleic acids are prepared by a method selected from the group consisting of mRNA isolation from a cell, in vitro transcription or chemical synthesis.

In yet another embodiment, the nucleic acids encode two or more different polypeptides.

In still another embodiment, the isolated nucleic acids are selected from the group consisting of RNA, DNA and combinations thereof.

In another embodiment, the RNA is selected from the group consisting of mRNA, siRNA, miRNA, hnRNA, tRNA and combinations thereof.

In yet another embodiment, the isolated nucleic acids comprise a mixture of different RNAs encoding two or more different polypeptides, wherein the relative abundance of each different RNA is essentially the same as the relative abundance of each different RNA in a second cell that is in a different physiological state than the irradiated cell.

In another embodiment, the isolated nucleic acids further comprise an inhibitory nucleic acid.

In one embodiment, the laser is a titanium sapphire laser.

In still another embodiment, the fluid medium is a liquid.

In still another embodiment, the cell is bathed with the fluid medium comprising two or more isolated nucleic acids at a discrete location on the cell's surface.

The present invention also encompasses a method of locally transfecting a cell, the method comprising radiating the cell with a laser, wherein the cell is in a fluid medium comprising a nucleic acid, wherein the laser porates the cellular membrane of the cell and the nucleic acid enters the cell, thereby locally transfecting the cell.

In one embodiment, the cell comprises a cellular process.

In another embodiment, the cellular process is a dendrite.

In one embodiment, the laser is a titanium sapphire laser.

In yet another embodiment, the fluid medium is a liquid.

In still another embodiment, the nucleic acid is an RNA.

In another embodiment, the RNA is selected from the group consisting of mRNA, siRNA, miRNA, hnRNA, tRNA and combinations thereof.

In one embodiment, the cell is a single cell.

The present invention also includes a kit for transferring a multigenic phenotype to a cell, the kit comprising a mixture of mRNA isolated from a cell, wherein the mixture of mRNA comprises one or more isolated mRNAs encoding two or more polypeptides, and an instructional material for the use thereof.

Also provided is a kit for transferring a multigenic phenotype to a cell, wherein the kit comprises a mixture of nucleic acids, wherein the mixture is phenotype-converting nucleic acid and an instructional material for the use thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1A depicts the recipient neuron cell bathed in a solution comprising mRNA. FIG. 1B depicts the recipient cell bathed in a discrete location (area with black dots) on its surface with a solution containing mRNA. The cell is photoporated with a laser within the discrete dots. Expression of mRNA is indicated in both figures by an area of solid black.

FIGS. 3A to 3D are images of a representative rat hippocampal neuron cell before and 2 weeks after phototransfection. FIG. 3A depicts a neuron with extensive neuronal processes before phototransfection. The soma is indicated by the arrow. FIGS. 3B-3D are images of a neuron cell 2 weeks after phototransfection with mRNA from rat astrocytes. FIG. 3B is a differential interference contrast (DIC) image depicting the retraction of neuronal processes in the phototransfected cell. The soma is indicated by the arrow. FIG. 3C is an image of the phototransfected cell in FIG. 3B stained with DAPI, which indicates the location of the cell nucleus. The nucleus is indicated by the arrow. FIG. 3D is an image that depicts the glial fibrillary acidic protein (GFAP) immunoreactivity of the phototransfected neuron cell in FIG. 3B. The soma is indicated by the arrow. GFAP was detected in fixed cells by incubation with mouse anti-GFAP antibody and then Cy3-conjugated goat anti-mouse antibody to detect GFAP.

FIG. 4A depicts a rat hippocampal neuron cell before phototransfection. FIG. 4B depicts the same neuron cell 3 weeks after phototransfection with mRNA from rat astrocytes. The image depicts the GFAP immunoreactivity of the phototransfected cell, located within the white dotted box. Fixed cells were incubated with mouse anti-GFAP antibody and then Alexa 546-fluoresin-conjugated goat anti-mouse antibody to detect GFAP.

FIG. 5A is a DIC image of the two cells (indicated by arrows), depicting the retraction of the neuronal processes. FIG. 5B depicts the GFAP immunoreactivity of the same two phototransfected cells (indicated by arrows). Fixed cells were incubated with mouse anti-GFAP antibody and then Alexa 546-fluoresin-conjugated goat anti-mouse antibody.

FIG. 6A depicts two cells (circled with white dotted lines and labeled Cell 1 and Cell 2), loaded with a calcium indicator. This image is representative of the baseline signal for each cell. FIG. 6B shows the response of the same two cells to stimulation with glutamate (100 µM). FIG. 6C depicts response of the same two cells to stimulation with potassium (50 mM). FIG. 6D depicts the cells recovering baseline signal after the potassium was washed from the cells. FIG. 6E is a graph of the calcium signaling image data. Signaling is measured as the change in fractional fluorescence ($\Delta F/Fo$) as a function of time.

DETAILED DESCRIPTION OF THE INVENTION

Figure 1A:
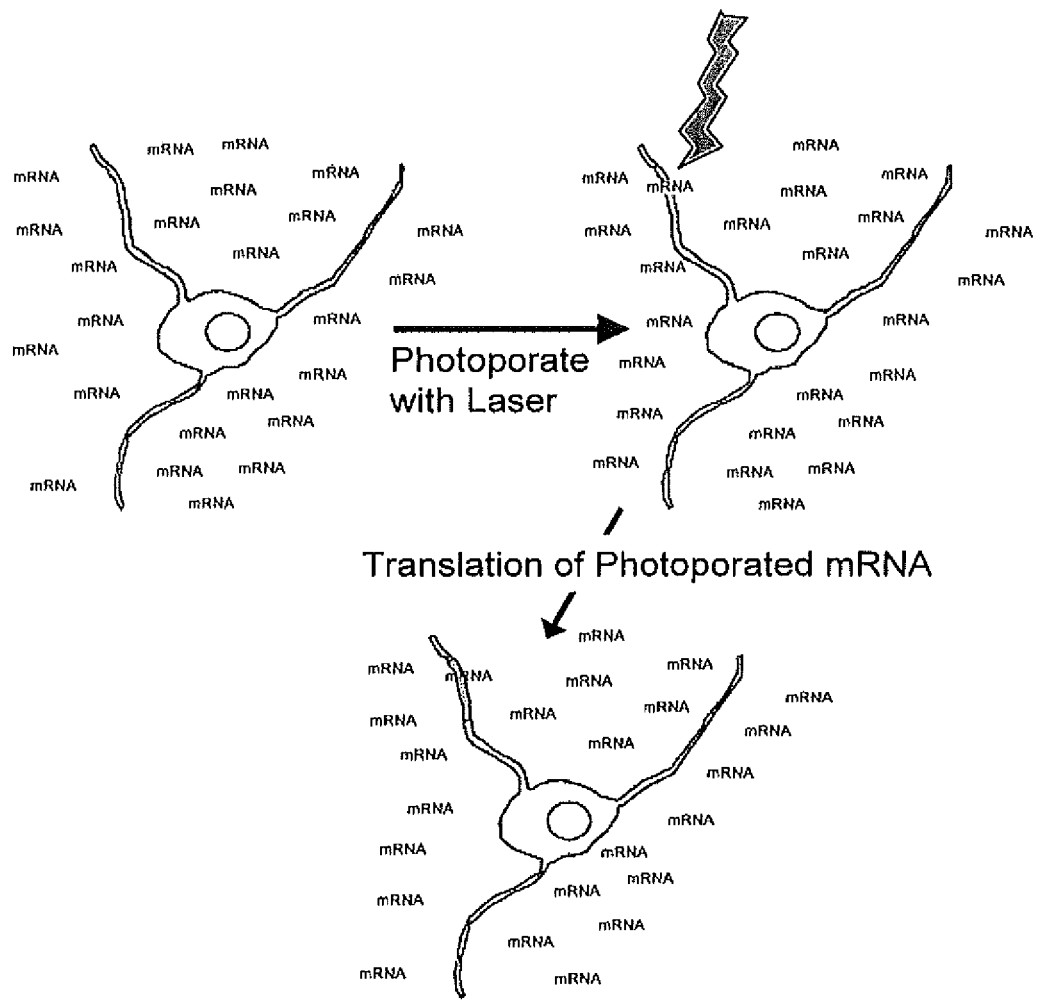
FIGS. 1A and 1B are schematic images of a laser inducing a small transient hole in a neuron cell membrane through which nucleic acid is introduced into the cell and translated into a protein. The images depict non-limiting embodiments in which the nucleic acid is mRNA.

The present invention encompasses methods to transfect mixtures of nucleic acids into a cell such that the nucleic acids are expressed in the cell, resulting in a multigenic effect in the cell. Specifically, the present invention comprises methods for transferring a multigenic phenotype to a cell by introducing a mixture of nucleic acids, such as RNA and/or DNA, into a cell to produce a multigenic phenotype in the cell. The nucleic acids can include, without limitation, mRNA, siRNA, microRNA, tRNA, hnRNA, total RNA, DNA, and the like, such that the introduction of these nucleic acids into a cell and the subsequent expression of these nucleic acids results in a combined phenotype due to the multiple expression of these nucleic acids and their interactions with each other. Unlike expression systems known in the art, where one or only a few nucleic acids are expressed, the methods of the present invention permit the expression of multiple nucleic acids essentially simultaneously, resulting in an expression system closely mirroring the interaction of various nucleic acids and their expression products in a natural environment. Thus, the present invention permits the introduction of a complex mixture of nucleic acids into a cell to produce a multigenic effect, thereby illuminating the phenotype of a cell, tissue or animal in which various nucleic acids and the proteins expressed therefrom are interacting, competing, and otherwise producing a phenotype.

The methods of the present invention are accomplished by transfecting nucleic acid into live cells. Specifically, the present invention includes methods for inducing a multigenic effect in a cell using laser-aided poration of live cell membranes coupled with bath application of mRNA in order to transfect a mixture of nucleic acids into a live cell. Further, the present method not only allows highly location-specific transfection of a cell, it is also not detrimental to cellular function or viability.

The present invention permits the transfection of nucleic acid, preferably mRNA and/or DNA into a cell with accurate control of the amount of nucleic acid entering the cell, thus allowing the skilled artisan to mimic the expression level of nucleic acid in a cell under desired conditions, as disclosed elsewhere herein. That is, the present invention allows the skilled artisan to accurately control the level of nucleic acid transfected into a cell by modulating the concentration of nucleic acid in the extracellular environment of the cell. Further, the precise amount of nucleic acid transfected into a cell can be modulated through regulation of laser intensity, pore size and number, and duration of membrane opening.

In addition, the present invention permits transfection of nucleic acid into a specific process of a cell to determine the capability of that process to transcribe and/or translate a nucleic acid, as well as to determine the effect expression of a protein has on the remainder of the cell. The nucleic acid introduced may encode a single product or may comprise a mixture of nucleic acids encoding two or more products and preferably, two or more polypeptides. Cells and their processes contemplated by the present invention include, but are not limited to, the microvilli of adsorptive epithelial cells, cilia of ciliated epithelial cells, the stereocilia of hair cells, the cellular processes linking osteoblasts, the axons of neurons and the dendrites of neurons. Other cells containing processes are known in the art.

The methods of the present invention are not limited to cells, but can further include live slices of tissue and live animals, preferably mammals, as disclosed elsewhere herein. The methods of the present invention can further comprise other non-mammalian cells eukaryotic cells and prokaryotic cells, such as bacterial cells, yeast cells, plant cells, protozoa, insect cells, fungal cells, including filamentous and non-filamentous fungi, and the like.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, a "destination phenotype" refers to a phenotype of interest that is induced in a recipient cell by the introduction therein of a mixture of nucleic acids.

The phenotype of interest may be any phenotype. For example, a destination phenotype may be a morphological change, such as the retraction of neuronal processes in a recipient cell that is a neuron. A destination phenotype may be a physiological change, such as the presence of voltage-gated calcium receptors in a recipient cell that is an astroglial cell. A destination phenotype may comprise more than one phenotypic change and may even cause the cell to assume characteristics of a different tissue type from its original tissue type.

The phrase "phenotype-converting nucleic acid" refers herein to a mixture of nucleic acid that is capable of establishing a destination phenotype in a recipient cell. Phenotype-converting nucleic acid is not limited to the empirical content of RNA in a donor cell, but rather, encompasses the relative abundance of each RNA with respect to each in a population of RNAs such that the population of RNAs are necessary and sufficient to induce a destination phenotype in a recipient cell.

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A "fluid medium" or "fluid media" is used herein to refer to a form of matter, such as air, liquid, solid or plasma, preferably liquid, that is capable of flowing.

An "isolated cell" refers to a cell which has been separated from other components and/or cells which naturally accompany the isolated cell in a tissue or mammal.

As applied to a protein, a "fragment" of a polypeptide, protein or an antigen, is about 6 amino acids in length. More preferably, the fragment of a protein is about 8 amino acids, even more preferably, at least about 10, yet more preferably, at least about 15, even more preferably, at least about 20, yet more preferably, at least about 30, even more preferably, about 40, and more preferably, at least about 50, more preferably, at least about 60, yet more preferably, at least about 70, even more preferably, at least about 80, and more preferably, at least about 100 amino acids in length amino acids in length, and any and all integers there between.

A "genomic DNA" is a DNA strand which has a nucleotide sequence homologous with a gene as it exists in the natural host. By way of example, a fragment of a chromosome is a genomic DNA.

As used herein, an "inhibitory nucleic acid" refers to an siRNA, a microRNA, an antisense nucleic acid or a ribozyme.

As used herein, "locally transfecting" a nucleic acid refers to introducing a nucleic acid into a region of cytoplasm that is not the entirety of the cytoplasm of a cell optionally comprising a cellular process.

As used herein, "porate" or "porates" refers to creating a hole in a surface through which compounds can pass.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are completely or 100% homologous at that position. The percent homology between two sequences is a direct function of the number of matching or homologous positions, e.g., if half (e.g., five positions in a polymer ten subunits in length) of the positions in two compound sequences are homologous then the two sequences are 50% identical, if 90% of the positions, e.g., 9 of 10, are matched or homologous, the two sequences share 90% homology. By way of example, the DNA sequences 5'ATTGCC3' and 5'TATGGC3' share 50% homology.

In addition, when the terms "homology" or "identity" are used herein to refer to the nucleic acids and proteins, it should be construed to be applied to homology or identity at both the nucleic acid and the amino acid sequence levels.

The term "multigenic phenotype" is used herein to refer to a phenotype in a cell, tissue or animal that is mediated by the expression or lack of expression of two or more nucleic acids encoding a protein, wherein the nucleic acids are exogenously provided to the cell, tissue or animal.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well, A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"Phototransfection" is used herein to refer to a process by which a hole is created in a barrier, such as a cell membrane, using a photon source, such as a laser, and two or more nucleic acids, wherein the nucleic acids encode different polypeptides, are inserted into a cell through the hole in the cell membrane.

By "tag" polypeptide is meant any protein which, when linked by a peptide bond to a protein of interest, may be used to localize the protein, to purify it from a cell extract, to immobilize it for use in binding assays, or to otherwise study its biological properties and/or function.

It is understood that any and all whole or partial integers between any ranges set forth herein are included herein.

Description

The present invention provides methods of introducing mixtures of nucleic acids into a recipient cell to produce a multigenic effect in the recipient cell. The present invention comprises transfecting a nucleic acid, preferably RNA and/or DNA, even more preferably mRNA, locally into a recipient cell. The recipient cell may be any type of cell. A recipient cell may be an eukaryotic cell or a prokaryotic cell. When the cell is an eukaryotic cell, the cell is preferably a mammalian cell, including but not limited to human, non-human primate, mouse, rabbit, rat, goat, guinea pig, horse cell, and the like. A non-mammalian eukaryotic cell includes a yeast cell, a plant cell, an insect cell, a protozoan cell and a fungal cell, including filamentous and non-filamentous fungi. When the cell is a prokaryotic cell the cell is a bacterial cell. Preferably, the recipient cell is a tissue-specific cell, more preferably a mammalian tissue-specific cell and more preferably still, a human tissue-specific cell. Non-limiting examples of cells suitable as recipient cells include epithelial cells, neurons, fibroblasts, embryonic fibroblasts, keratinocytes, adult stem cells, embryonic stem cells, and cardiomyocytes. In embodiments of the invention drawn to phenotype conversion, phenotypically-pliable cells are preferable. Phenotypically-pliable cells are cells whose phenotype is amenable to changing under the conditions of the method of the invention. Non-limiting examples of phenotypically-pliable cells include neurons, fibroblasts, embryonic fibroblasts, adult stem cells and embryonic stem cells. Preferably, the cell is a neuron, and comprises a cellular process such as a dendrite, and the nucleic acid is RNA, even more preferably, mRNA, Even more preferably, the nucleic acid comprises a complex mixture of mRNAs, including mRNAs encoding two or more different proteins.

As disclosed elsewhere herein, the present invention comprises a method for transferring a multigenic phenotype to a recipient cell. Preferably, the multigenic phenotype is transferred by isolating two or more nucleic acids from a first cell, and transfecting a second cell with those two or more nucleic acids. In some embodiments, the two or more nucleic acids encode different polypeptides. In other embodiments, the nucleic acids are non-coding RNAs or other non-coding nucleic acids. In yet other embodiments, the nucleic acids comprise a mixture of coding and non-coding nucleic acids. In yet other embodiments, nucleic acid from a first recipient cell are subsequently transferred into a second recipient cell. The present invention can further comprise chemically synthesizing two or more nucleic acids that encode different polypeptides. Methods for chemically synthesizing a nucleic acid are disclosed elsewhere herein and can include in vitro transcription.

In the method of the invention, nucleic acid is transferred into a cell to initiate phenotype conversion in the recipient cell. As used herein, phenotype conversion comprises a change in at least one of gene expression, protein expression, immunological markers, morphology, physiology, synthesis of bioproducts (e.g., dopamine) and membrane lipid composition. Preferably, the change yields a phenotype associated with or indicative of the cell from which the transfected RNA or DNA is obtained. Preferably, phenotype conversion in the recipient cell comprises two or more changes. More preferably, phenotype conversion comprises three or more changes. In one embodiment, phenotype conversion comprises a change in physiology. In another embodiment, phenotype conversion comprises a change in morphology and a change in physiology of the recipient cell.

Phenotype conversion in the recipient cell is maintained stably for extended periods of time. In one embodiment, phenotype conversion is stable for at least about 1 day, 2 days, 3 days, 4 days, 5 days, 6 days, 7 days, 8 days, 9 days, 10 days, 11 days, 12 days, 13 days, or more. In one embodiment, phenotype conversion is stable for at least about 1 week, 2 weeks, 3 weeks, 4 weeks, or more. In another embodiment, phenotype conversion is stable for at least about 1 month, 2 month, 3 months or more. In preferred embodiments, phenotype conversion is stable for the duration of the recipient cell's lifespan or the lifespan of a culture derived from the recipient cell.

The present invention is not limited to transferring a multigenic phenotype with only two nucleic acids encoding different polypeptides. The present invention can further comprise transferring a multigenic phenotype using 3 or more, 5 or more, 10 or more, 20 or more, 40 or more, 50 or more, 75 or more, 100 or more, 200 or more, or the total RNA or mRNA from a cell, tissue or animal wherein the RNA or mRNA encodes different polypeptides.

The present invention can further comprise locally transfecting a cell comprising a cellular process. Such a cellular process includes, but is not limited to, a dendrite, an axon, a microvilli, a cilia, a stereocilia, a process, an astrocytic process, and the like. As demonstrated herein, this method advantageously permits the introduction of a desired amount of nucleic acid into one or more local sites, permitting the controlled and localized production of protein in physiological amounts, resulting in a multigenic effect in a cell. This method thus allows specific localization of exogenously applied nucleic acid, preferably mRNA, without resorting to severing the cellular process from the cell to which it is attached (Kacharmina, et al., 2000, Proc. Nat'l Acad. Sci. USA, 97:11545-11550). Further, the present method permits the expression of a mixture of nucleic acid, thus resulting in the expression of multiple proteins and a multigenic phenotype in the cell.

The present invention further comprises methods for phototransfecting a live slice of tissue or a live animal. Methods for sustaining the cellular processes in the cells comprising a live slice of tissue are known in the art. As a non-limiting example, live slices can be refrigerated and perfused with natural or artificial fluids, such as artificial spinal fluid, artificial central nervous system fluid, and buffers disclosed elsewhere herein. Methods for the manipulation of live slice cultures are described in, for example, Roelandse, et al. (2004, J. Neuroscience, 24: 7843-7847); and Chen, et al. (2005, Magn. Reson. Med. 53: 69-75).

Methods for phototransfecting a live animal, preferably a mammal, are performed using the methods described herein combined with methods of animal and human surgery known in the art. Exemplary surgical procedures contemplated for use with the methods of the invention include cardiac catherization, angioplasty, arthroscopy, laproscopy, tumor resection, surgical placement of a therapeutic implant and the like. Mammals contemplated in the present invention include, but are not limited to, mice, rabbits, rats, goats, guinea pigs, humans, and the like.

As a non-limiting example, a laser is applied to a tissue in a live animal to phototransfect the tissue in the live animal with one or more nucleic acids. The nucleic acid is introduced to the animal using methods disclosed elsewhere herein, such as through a microscope or an optical fiber or endoscopy. The expression of a polypeptide phototransfected using the methods of the present invention is monitored using methods of detecting protein expression known in the art, such as Western blots, immunocytochemistry, in situ protein detection, and the like. Methods for using a laser to manipulate animal tissues are well known in the art and are described in, for example, Dang, et al. (2005, Exp Dermatol., 14: 876-882).

Figure 1B:
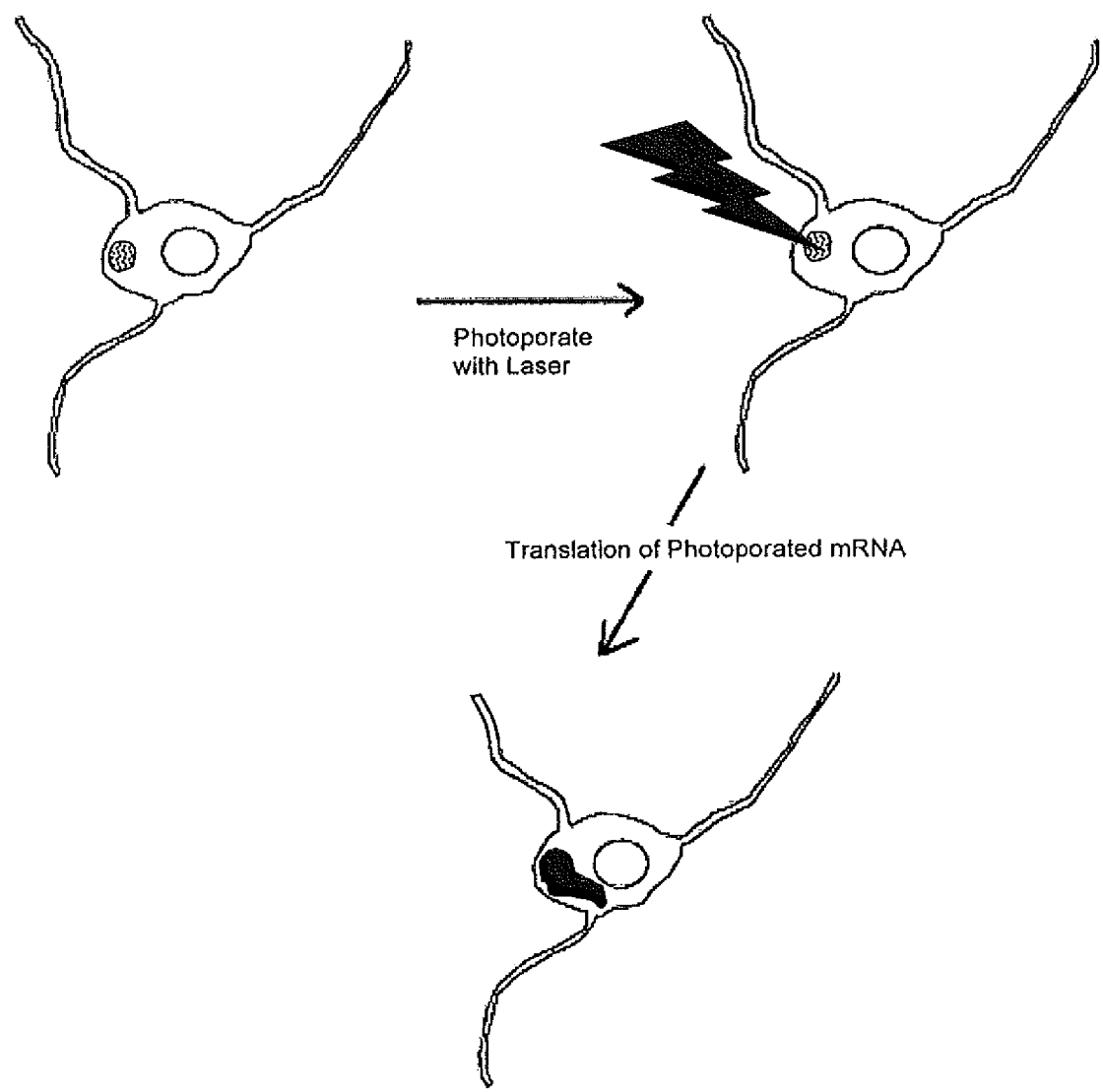

The methods disclosed herein comprise introducing a nucleic acid, preferably an RNA and more preferably mRNA, siRNA, miRNA, hnRNA, tRNA, non-coding RNAs and combinations thereof, including but not limited to total RNA, to a cell that optionally comprises a cellular process, preferably a neuron comprising a dendrite, and phototransfecting the cell at one or more sites on the cell membrane. The cell is preferably a primary cell culture or in slice culture. The cell optionally comprising a cellular process can be phototransfected at any site. Preferably, the site is on a cellular process, such as a dendrite, or the cell body, such as the soma. The nucleic can be provided to the cell comprising a cellular process by any method known to the skilled artisan, and is preferably provided by means of a nucleic acid bath comprising a mixture of nucleic acids, disclosed elsewhere herein. A nucleic acid bath is a solution comprising a nucleic acid of interest in which a cell is bathed. In one embodiment, bath application of the cell comprises surrounding the cell with a solution comprising nucleic acid, thus bathing the entire cell. The cell is then irradiated with a laser at one or more sites located anywhere on the cell. See FIG. 1A. In another embodiment, bath application comprises bathing a discrete portion or portions of a live cell, for instance, by applying a solution comprising nucleic acid to a discrete location on the surface of the cell. The cell is then irradiated one or more times within the discrete location or locations that was bathed. See FIG. 1B. The discrete location bath is advantageous because it creates a greater mRNA concentration gradient, which allows mRNAs to diffuse more efficiently through the temporary poration holes into the porated cell. It also requires less mRNAs (e.g., 0.3 μg) than the bath application (e.g., 20 μg). In either case, the solution is appropriately buffered and is of the proper pH to maintain the structural integrity of the cell to be phototransfected.

A nucleic acid of interest suitable for use in the method of the invention may be of any size. For instance, a nucleic acid of about 800 nucleotides and a nucleic acid of about 3000 nucleotides have been successfully phototransfected into cells comprising a cellular process using the inventive procedure. However, the methods of the present invention are not limited to a nucleic acid, preferably an RNA, of the sizes disclosed herein. The present invention comprises phototransfecting a nucleic acid of about 30 bases, even more preferably, about 50 bases, yet more preferably, about 75 bases, even more preferably, about 100 bases, yet more preferably, about 75 bases, even more preferably, about 100 bases, yet more preferably, about 150 bases, even more preferably, about 200 bases, yet more preferably, about 300 bases, even more preferably, about 500 bases, yet more preferably, about 750 bases, even more preferably, about 1000 bases, yet more preferably, about 1500 bases, even more preferably, about 2000 bases, yet more preferably, about 2500 bases, even more preferably, about 3000 bases, in length. Even more preferably, the present invention comprises transfecting, preferably by phototransfection, a mixture of RNAs encoding different proteins and of different molecular weights.

The present invention is useful for transfecting homogenous or heterogeneous nucleic acids into a cell. Specifically, the methods disclosed herein can be used to transfect RNA, DNA, or both into a cell at physiologically relevant amounts. Further, the present invention can be used to introduce a mixture of RNAs encoding different proteins, a mixture of DNAs encoding different proteins, or a mixture of both RNAs and DNAs into a cell in order to determine the multigenic effects and interactions of various nucleic acids. Mixtures may also comprise non-coding nucleic acids.

As a non-limiting example, a nucleic acid expression profile of a cell in a desired physiological state (e.g. during differentiation, in a disease state, after treatment with a pharmaceutical, toxin or other compound) and a nucleic acid expression profile of a cell in another physiological state (e.g. the same cell type pre- or post-differentiation, not in a disease state, or before treatment with a pharmaceutical, toxin or other compound) can be obtained using techniques for RNA isolation known in the art and disclosed elsewhere herein. The cDNA clones of these RNAs can be generated, reflecting the altered RNA abundances of the differing physiological states, or the RNA can be transfected into a cell without first reverse transcribing the RNA to cDNA. These RNA can be mixed according to the same ratios and abundances indicated by the nucleic acid expression profiles of the cells in differing physiological states. These nucleic acid mixtures are then transfected into a cell using the phototransfection methods disclosed herein. The methods of the present invention permit the local transfection of a cell, and therefore the nucleic acid mixture can be locally transfected to a specific part of a cell, such as the soma, an astrocytic process, a dendrite, or another cellular process, or the nucleic acid mixture can be generally transfected into a cell by phototransfecting any portion of the cell. Using the methods of the present invention, and the physiologically relevant mixtures of nucleic acids described herein, once the mixture of nucleic acids is expressed in a cell, the phenotype of the physiological state can be replicated in a cell or a cellular process, thus allowing the skilled artisan to observe the phenotype transfer in a cell or cellular process.

Nucleic acid may be obtained from any cell of interest in any physiological state. The donor cell may be any type of cell. A donor cell may be an eukaryotic cell or a prokaryotic cell. When the cell is an eukaryotic cell, the cell is preferably a mammalian cell, including but not limited to human, non-human primate, mouse, rabbit, rat, goat, guinea pig, horse cell, and the like. A non-mammalian eukaryotic cell includes a yeast cell, a plant cell, an insect cell, a protozoan cell and a fungal cell, including filamentous and non-filamentous fungi. When the cell is a prokaryotic cell the cell is a bacterial cell. Non-limiting examples of cells from which nucleic acid may be obtained include astrocytes, cardiomyocytes, neonatal cardiomyocytes, embryonic stem cells and neurons. RNA from any donor cell of interest can be phototransfected into any recipient cell in the method of the invention. Preferably, donor cells are of the same species as the recipient cells. Donor cells may be from the same individual as the recipient cell, or from a different individual. Donor cells may originate from the same germinal layer (e.g., ectoderm) as the recipient cell (e.g. both arise from ectoderm germ layer), or from a different germinal layer (e.g., one cell arises from ectoderm and the other arises from endoderm germ layer). Donor cells may be the same cell type as the recipient cell but at a different stage of differentiation, exposed to a candidate therapeutic, exposed to a toxin or pathogen, diseased. In yet other embodiments, a donor cell may be a recipient cell. For instance, nucleic acid from a donor cell is transferred into a first recipient cell. Nucleic acid from the first recipient cell is then subsequently transferred into a second recipient cell. In one aspect, the first and second recipient cells are in different physiological states. In another aspect, the first and second recipient cells are the same type of cell. As described elsewhere herein, RNA obtained from a cell may be used to transfect a cell, or may be used as a template to create cDNA. The cDNA may be used in in vitro transcription methods to amplify some or all of the RNA, which is then used in the method of the invention.

As a non-limiting example, the total RNA from a neuronal stem cell or other progenitor neuronal cell can be isolated from such a cell using techniques known in the art and disclosed elsewhere herein. The total RNA can then be processed using various methods known in the art for isolating mRNA, such as isolation of mRNA using complementary poly-dT nucleic acids, which can be conjugated to beads or a column. The mRNA is then transfected into a recipient cell using the methods disclosed herein. The recipient cell then expresses the mixture of mRNA isolated from the neuronal stem cell and replicates the multigenic effect of the differential gene translation and regulation characteristic of a developing neuronal stem cell. The present invention is not limited to neuronal stein cells however, and can be used to determine the transferred multigenic phenotype of any type of developing or developed cell, provided that the total RNA and mRNA are isolated from the cell.

As an alternative non-limiting example, the total RNA from a cell treated with a compound, such as a drug, a peptide, a cytokine, an antibody, a mitogen, a toxin, or other compounds known in the art, can be isolated using the methods disclosed herein and known in the art. The mRNA from that cell can then be transfected into another cell type using the methods disclosed herein, thus transferring the multigenic phenotype of the cell treated with a compound to another cell, thus enabling the rapid and specific determination of that compound on another cell type.

In another non-limiting embodiment of the present invention, the total RNA from a diseased cell, such as a tumor cell, a cell harboring an intracellular pathogen, a cell from a patient with an autoimmune disease, and the like, can be isolated from the diseased cell. The mRNA from that cell can be isolated using, for example, poly-dT isolation techniques. The mRNA from the diseased cell is transfected into another cell using the methods of the present invention, thus transferring the multigenic phenotype of the diseased cell to another cell, providing a more accurate picture of the role interacting nucleic acids and their encoded proteins have in the phenotype of a cell.

The present invention can further comprise the use of a nucleic acid from a cell or a population of cells of homogeneous or heterogeneous types. The present invention can further comprise the use of a nucleic acid, preferably mRNA, defined by the expression profile of a cell as determined using methods well known in the art, including, but not limited to, a gene array profile, total RNA, total mRNA, and the like. An expression profile is used to determine the relative abundances of mRNA in a cell. The expression profile is then used as a template to determine the relative abundances of mRNA in the physiological state of the cell from which the expression profile was made. A population of mRNA with the same relative abundance as in the cell for which expression has been profiled is produced using the methods disclosed elsewhere herein, including mRNA isolation, in vitro transcription or chemical synthesis. The mRNA is then phototransfected into the cell using the methods described elsewhere herein, thereby transferring the phenotype of the cell from which the expression profile was made to another cell, tissue or animal.

In another embodiment, population of mRNA reflecting the relative abundance of a cell in a particular physiological state further comprises mRNA encoding one or more polypeptides that facilitate phenotype conversion. For instance, the mRNA obtained from a neuronal cell may be supplemented with mRNA encoding proteins that stimulate exocytosis and is then phototransfected into a non-neuronal recipient cell.

The present invention further comprises the sequential phototransfection of a cell. Sequential phototransfection is used herein to refer to a process in which a cell is phototransfected at a first time point, and then phototransfected at a second or subsequent time point. As an example, a cell can be phototransfected on day 1, the result of which is that one or more nucleic acids are introduced into the cell. These nucleic acids can be expressed by the cellular translation complexes or remain silent, or can be inhibited using an inhibitory nucleic acid as disclosed elsewhere herein. On day 2, the same cell can be phototransfected again, transfecting one or more of the same or dissimilar nucleic acids to the same cell. The present invention is not limited to phototransfection separated by a day however. Sequential phototransfection can occur with minutes, hours, days, weeks or months between a first time point and a second time point, provided the phototransfection occurs to the same cell. Thus, the sequential phototransfection methods of the present invention are limited only by the lifespan of the cell.

The sequential phototransfection methods of the present application are useful for, among other things, analyzing temporal gene expression in a cell, analyzing the multigenic effects of a protracted developmental process, and determining the relationship of genotype to phenotype over the course of the viable life span of a cell. Sequential phototransfection using the same nucleic acids also increases the robustness of expression of the phototransfected nucleic acids.

The embodiments of the inventions disclosed herein are not limited to mRNA. The present invention can further comprise reverse transcribing mRNA into cDNA, then transfecting the cDNA into a cell The present invention is not limited to the use of RNA and mRNA. A mixture of DNA and RNA can be used in the methods of the present invention to determine the effects of transient (RNA) as well as prolonged (DNA integration into the genome) gene expression in a cell.

When a mixture of nucleic acids, such as a mixture of RNAs is phototransfected into a cell, subpopulations of that mixture can be phototransfected into a cell to determine the core set of RNAs responsible for a given phenotype. As a non-limiting example, when the total RNA is isolated from a cell in a certain physiological state and mRNA is isolated from that population of total RNA, specific subpopulations of the isolated mRNA can be transfected into a cell to establish the core mRNAs responsible for that phenotype. The present embodiment can also be performed with cDNA produced from mRNA. Specific populations of mRNA can be identified using sequence homology data or other characteristic features known in the art and available from various databases, such as GenBank® (United States Department of Health and Human Services, Bethesda Md.).

Alternatively, the mRNA from a cell can be isolated and transfected into a cell using the methods of the present invention, and an siRNA, microRNA, antisense nucleic acid or ribozyme (collectively referred to as an inhibitory nucleic acid) can be transfected along with the mRNA, resulting in silencing and/or inhibition of an mRNA. Silencing an mRNA permits one of skill in the art to identify, for instance, the core mRNA(s) responsible for a multigenic phenotype. In addition, the present invention allows the replication of a phenotype in another cell without the step of determining the nucleic acid expression profile of a cell in a physiological state. The nucleic acid, preferably RNA, from a cell in a specific physiological state, such as a certain differential or disease state, can be isolated. Using the methods of the present invention, the RNA, or a cDNA of the RNA, can be transfected into a cell in order to analyze the phenotype in the transfected cell once the nucleic acid has been expressed. The nucleic acid, preferably RNA, can be the total RNA from a cell, or a subpopulation of the RNA, such as mRNA.

To assess the effect of expression of the transfected nucleic acids, cells transfected in accordance with the method of the invention can be examined using methods known in the art. Assessments may be made, for example, of phenotypic changes, mRNA expression, protein expression and functional assays. Examples of such analyses include, but are not limited to, cell morphology, presence and absence of immunological markers, RT-PCR, expression profiling, mRNA abundance measurements, immunocytochemistry analysis (ICC) for specific proteins, cell viability, and cell-specific activities, such as cell division-mitosis and electrophysiology.

In some embodiments, the present method further comprises inhibiting transcription factors in the transfected cell, thus preventing competition between expression of endogenous and exogenous mRNAs and the proteins encoded thereby. A transcription factor can be inhibited using an inhibitory nucleic acid or compounds that inhibit transcription factors, such as a protease, or SP100030 (Huang et al., 2001, Br. J. Pharmacol., 134: 1029-1036). Other agents useful for inhibiting transcription in a recipient cell include, but are not limited to, α-amanitin, trichostatin A (TSA; a histone deacetylase inhibitor), tubulin depolymerizer and actin depolymerizer. Preferably, a recipient cell is contacted with one or more transcription inhibition agents prior to transfection. Preferably, the cell is contacted between about 30 minutes and about 80 hours, preferably between about 30 minutes and about 60 hours and more preferably, between about 6 hours to about 48 hours, prior to transfection. In a non-limiting example, a rat hippocampal neuron is contacted with TSA and α-amanitin at a final concentration of 100 nM and 100 microgram per nil in a neuronal cell medium, respectively. The neuron is then irradiated between about 24 to about 55 hours later. In some embodiments of the invention including sequential phototransfection of a recipient cell, the recipient cell is preferably not contacted with a transcription inhibitor subsequent to the first phototransfection.

Figure 2:
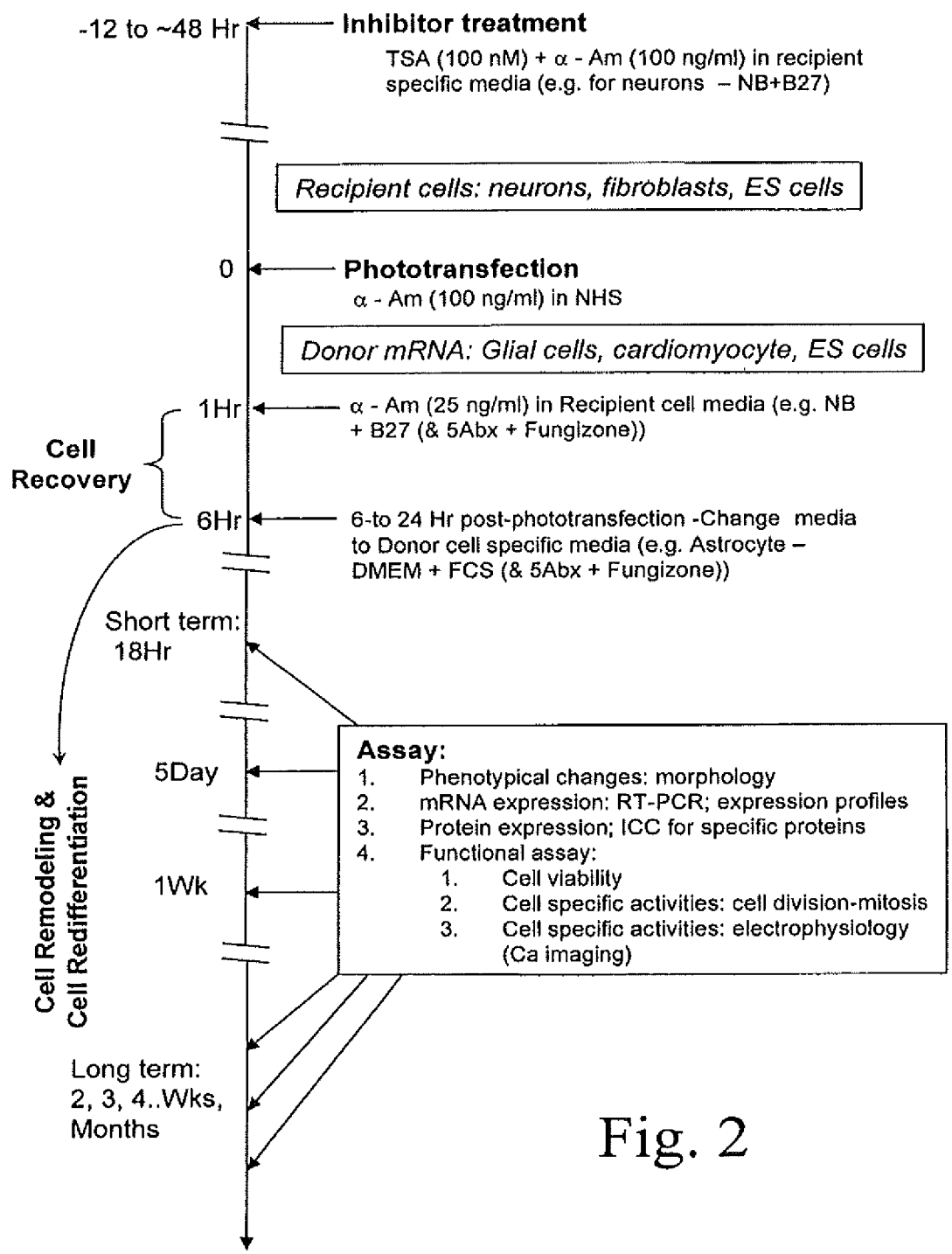
FIG. 2 is an exemplary timeline for an embodiment of the invention. The timeline depicts the treatment of recipient cells (e.g., neurons) before, during and after phototransfection with a mRNA obtained from donor cells (e.g., glial cells). Also shown are possible assays for assessing the effect of expression of glial mRNA in such phototransfected neuron cells.

FIG. 2 depicts a non-limiting example of a timeline for phototransfection of a recipient cell, for instance a neuron, with mRNA from a recipient cell, for instance, a glial cell. The timeline depicts a period of transcription inhibitor treatment, a period of phototransfection cell recovery and a period cell remodeling and redifferentiation. Possible changes in media are indicated, including transfer from a recipient-cell-specific medium to a donor-cell-specific medium. Such media changes are useful, for instance, for supporting phenotype conversion. Assays that may be used to characterize the remodeling and redifferentiation of the phototransfected recipient cell are enumerated in the box on the top right.

The present method can also be used for the specific and local transfection of an inhibitory nucleic acid, such as an siRNA, antisense nucleic acid or a microRNA (miRNA), using the methods of the present invention. Using the invention disclosed herein, the skilled artisan can specifically inhibit a cellular nuclear acid, especially those in cellular processes. Further, as disclosed elsewhere herein, an inhibitory nucleic acid can be used to identify the core nucleic acid(s) involved in a multigenic phenotype.

The present invention comprises inserting a nucleic acid into a cell. The methods of the present invention are amenable to a variety of nucleic acids, including various species of RNA (mRNA, siRNA, miRNA, hnRNA, tRNA, total RNA, combinations thereof and the like) as well as DNA. Methods for isolating RNA from a cell, synthesizing a short polynucleotide, constructing a vector comprising a DNA insert, and other methods of obtaining a nucleic acid to phototransfect into a cell are well known in the art and include, for example, RNA isolation, cDNA synthesis, in vitro transcription, and the like.

The nucleic acid compositions of this invention, whether RNA, cDNA, genomic DNA, or a hybrid of the various combinations, may be isolated from natural sources or may be synthesized in vitro. Techniques for nucleic acid manipulation are described generally in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York)., incorporated herein by reference. Nucleic acids suitable for use in the present method also include nucleic acid analogs. Examples of such analogs include, but are not limited to, phosphorothioate, phosphotriester, methyl phosphonate, short chain alkyl or cycloalkyl intersugar linkages, or short chain heteroatomic or heterocyclic intersugar ("backbone") linkages. In addition, nucleic acids having morpholino backbone structures (U.S. Pat. No. 5,034,506)

or polyamide backbone structures (Nielsen et al., 1991, Science 254: 1497) may also be used.

The methods of the present invention can comprise the use of a variety of nucleic acids, including DNA, RNA, a cDNA reverse transcribed from an mRNA, an RNA transcribed from that cDNA, a DNA amplified from the cDNA, an RNA transcribed from the amplified DNA, and the like. The present invention further comprises using single-stranded and double-stranded RNA and DNA molecules. Any coding sequence of interest can be used in the methods of introducing and translating a nucleic acid in a cell or in a cellular process, such as a dendrite. One of skill in the art will understand, when armed with the present disclosure, that a multitude of properties of a cellular process, and by association, of the attached cell, can be affected by the methods of the present invention. For instance, for studies of dendrite remodeling, any coding sequence for a protein involved in the growth, homeostasis or remodeling of a dendrite are useful in the methods of the invention. Non-limiting examples of such proteins include: cadherin, neurexin, synaptophysin, tubulin, microtubule associated proteins and actin.

In one embodiment of the present invention, the nucleic acid phototransfected into a cell is all or a portion of the total mRNA isolated from a biological sample. The term "biological sample," as used herein, refers to a sample obtained from an organism or from components (e.g., organs, tissues or cells) of an organism. The sample may be of any biological tissue or fluid. The nucleic acid (either genomic DNA or mRNA) may be isolated from the sample according to any of a number of methods well known to those of skill in the art. One of skill will appreciate that where alterations in the copy number of a gene are to be detected genomic DNA is preferably isolated. Conversely, where expression levels of a gene or genes are to be detected, preferably RNA (mRNA) is isolated.

Methods of isolating total mRNA are well known to those of skill in the art. For example, methods of isolation and purification of nucleic acids are described in detail in Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993) and Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993)).

Preferably, the total nucleic acid is isolated from a given sample using, for example, an acid guanidinium-phenol-chloroform extraction method and polyA$^+$ mRNA is isolated by oligo dT column chromatography or by using (dT)n magnetic beads. Commercially available products, such as TRIZOL and MICRO-FASTTRACK (Invitrogen™, Carlsbad, Calif.), are useful in extracting nucleic acid from a biological sample.

The mRNA can be locally transfected directly into a cell or a cellular process, or the sample mRNA can be reverse transcribed with a reverse transcriptase and a promoter comprising an oligo dT and a sequence encoding the phage T7 promoter to provide single stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro polymerization are well known to those of skill in the art (see, e.g., Sambrook, supra.; Van Gelder, et al., 1990, Proc. Natl. Acad. Sci. USA, 87: 1663-1667). Moreover, Eberwine et al. (1992, Proc. Natl. Acad. Sci. USA, 89: 3010-3014) provide a protocol using two rounds of amplification via in vitro transcription to achieve greater than $10^6$ fold amplification of the original starting material.

The present invention further comprises the use of in vitro transcription for phototransfection into a cell or cellular process. In vitro transcription comprises the production of dsRNA by transcribing a nucleic acid (DNA) segment in both directions. For example, the HiScribe™ RNAi transcription kit (New England Biolabs, Ipswich, Mass.) provides a vector and a method for producing a dsRNA for a nucleic acid segment that is cloned into the vector at a position flanked on either side by a T7 promoter. Separate templates are generated for T7 transcription of the two complementary strands for the dsRNA. The templates are transcribed in vitro by addition of T7 RNA polymerase and dsRNA is produced. Similar methods using PCR and/or other RNA polymerases (e.g., T3 or SP6 polymerase) can also be used and are known in the art.

The present invention further comprises the use of chemically synthesized nucleic acids for use in phototransfection. Oligonucleotides for use as probes can be chemically synthesized according to the solid phase phosphoramidite triester method first described by Beaueage, (1981, Tetrahedron Letts., 22:1859-1862) using an automated synthesizer, as described in Needham-VanDevanter, et al. (1984, Nucleic Acids Res., 12:6159-6168). Purification of oligonucleotides is by either native acrylamide gel electrophoresis or by anion-exchange HPLC as described in Pearson (1983, J. Chrom., 255:137-149). The sequence of the synthetic oligonucleotides can be verified using the chemical degradation method of Maxam (1980, in Grossman and Moldave, eds., Methods in Enzymology, Academic Press, New York, 65:499-560).

The present invention can further comprise the use of DNA in a process to locally transfect a cell or a cellular process via phototransfection. The DNA can be contained in a vector, such as those described herein.

The invention includes an isolated DNA encoding a protein operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

Expression of a protein in a cell or a cellular process phototransfected as disclosed herein may be accomplished by generating a plasmid or other type of vector comprising the desired nucleic acid operably linked to a promoter/regulatory sequence which serves to drive expression of the protein, with or without a tag, in cells in which the vector is introduced. Many promoter/regulatory sequences useful for driving constitutive expression of a gene are available in the art and include, but are not limited to, for example, the cytomegalovirus immediate early promoter enhancer sequence, the SV40 early promoter, as well as the Rous sarcoma virus promoter, and the like. Moreover, inducible and tissue specific expression of the nucleic acid encoding a protein can be accomplished by placing the nucleic acid encoding a protein under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In addition, promoters which are well known in the art which are induced in response to inducing agents such as metals, glucocorticoids, and the like, are also contemplated in the invention. Thus, it will be appreciated that the invention includes the use of any promoter/regulatory sequence, which is either known or unknown, and which is capable of driving expression of the desired protein operably linked thereto.

Selection of any particular plasmid vector or other DNA vector is not a limiting factor in this invention and a wide plethora of vectors are well-known in the art. Further, it is well within the skill of the artisan to choose particular promoter/regulatory sequences and operably link those promoter/regulatory sequences to a DNA sequence encoding a desired polypeptide. Such technology is well known in the art and is described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

The nucleic acids encoding a protein can be cloned into various plasmid vectors. However, the present invention should not be construed to be limited to plasmids or to any particular vector. Instead, the present invention should be construed to encompass a wide plethora of vectors which are readily available and/or well-known in the art.

The present invention further comprises locally transfecting an inhibitory nucleic acid, such as an antisense nucleic acid, an siRNA or an miRNA via phototransfection into a cell. An siRNA polynucleotide is an RNA nucleic acid molecule that interferes with RNA activity that is generally considered to occur via a post-transcriptional gene silencing mechanism. An siRNA polynucleotide preferably comprises a double-stranded RNA (dsRNA) but is not intended to be so limited and may comprise a single-stranded RNA (see, e.g., Martinez et al., 2002, Cell 110:563-74). The siRNA polynucleotide included in the invention may comprise other naturally occurring, recombinant, or synthetic single-stranded or double-stranded polymers of nucleotides (ribonucleotides or deoxyribonucleotides or a combination of both) and/or nucleotide analogues as provided herein (e.g., an oligonucleotide or polynueleotide or the like, typically in 5' to 3' phosphodiester linkage). Accordingly it will be appreciated that certain exemplary sequences disclosed herein as DNA sequences capable of directing the transcription of the siRNA polynucleotides are also intended to describe the corresponding RNA sequences and their complements, given the well established principles of complementary nucleotide base-pairing.

An siRNA may be transcribed using as a template a DNA (genomic, cDNA, or synthetic) that contains a promoter for an RNA polymerase promoter. For example, the promoter can be the U6 promoter or the H1 RNA polymerase III promoter. Alternatively, the siRNA may be a synthetically derived RNA molecule. In certain embodiments, the siRNA polynucleotide may have blunt ends. In certain other embodiments, at least one strand of the siRNA polynucleotide has at least one, and preferably two nucleotides that "overhang" (i.e., that do not base pair with a complementary base in the opposing strand) at the 3' end of either strand of the siRNA polynucleotide. In a preferred embodiment of the invention, each strand of the siRNA polynucleotide duplex has a two-nucleotide overhang at the 3' end. The two-nucleotide overhang is preferably a thymidine dinucleotide (TT) but may also comprise other bases, for example, a TC dinucleotide or a TG dinucleotide, or any other dinucleotide. The overhang dinucleotide may also be complementary to the two nucleotides at the 5' end of the sequence of the polynucleotide that is targeted for interference. For a discussion of 3' ends of siRNA polynucleotides see, e.g., WO 01/75164.

Preferred siRNA polynucleotides comprise double-stranded polynucleotides of about 18-30 nucleotide base pairs, preferably about 18, about 19, about 20, about 21, about 22, about 23, about 24, about 25, about 26, or about 27 base pairs, and in other preferred embodiments about 19, about 20, about 21, about 22 or about 23 base pairs, or about 27 base pairs. The siRNA polynucleotide useful in the present invention may also comprise a polynucleotide sequence that exhibits variability by differing (e.g., by nucleotide substitution, including transition or transversion) at one, two, three or four nucleotides from a particular sequence. These differences can occur at any of the nucleotide positions of a particular siRNA polynucleotide sequence, depending on the length of the molecule, whether situated in a sense or in an antisense strand of the double-stranded polynucleotide. The nucleotide difference may be found on one strand of a double-stranded polynucleotide, where the complementary nucleotide with which the substitute nucleotide would typically form hydrogen bond base pairing, may not necessarily be correspondingly substituted. In preferred embodiments, the siRNA polynucleotides are homogeneous with respect to a specific nucleotide sequence.

Polynucleotides that comprise the siRNA polynucleotides of the present invention may in certain embodiments be derived from a single-stranded polynucleotide that comprises a single-stranded oligonucleotide fragment (e.g., of about 18-30 nucleotides) and its reverse complement, typically separated by a spacer sequence. According to certain such embodiments, cleavage of the spacer provides the single-stranded oligonucleotide fragment and its reverse complement, such that they may anneal to form, optionally with additional processing steps that may result in addition or removal of one, two, three or more nucleotides from the 3' end and/or the 5' end of either or both strands, the double-stranded siRNA polynucleotide of the present invention. In certain embodiments the spacer is of a length that permits the fragment and its reverse complement to anneal and form a double-stranded structure (e.g., like a hairpin polynucleotide) prior to cleavage of the spacer, and optionally, subsequent processing steps that may result in addition or removal of one, two, three, four, or more nucleotides from the 3' end and/or the 5' end of either or both strands. A spacer sequence may therefore be any polynucleotide sequence as provided herein that is situated between two complementary polynucleotide sequence regions which, when annealed into a double-stranded nucleic acid, result in an siRNA polynucleotide.

The present method further comprises methods for introducing a nucleic acid into a cell. The method comprises phototransfecting a cell in the presence of a nucleic acid, preferably RNA and/or DNA, where the nucleic acid is in a fluid medium permitting the transfer of the nucleic acid from one side of the cell membrane to the other side of the cell membrane through a hole in the cell membrane. The fluid medium can comprise any medium having the buffering capacity and pH to support the viability of a cell and the stability of a nucleic acid molecule. Contemplated media include, but are not limited to, phosphate buffered saline, Tris, Tris-EDTA (TE) cell culture media, other aqueous mediums and buffers, and the like.

The number of nucleic acid molecules that enter the cell is influenced by the nucleic acid concentration in the nucleic acid bath, the size of the nucleic acid molecule, and laser intensity, e.g., the length of each laser pulse and the number of laser pulses delivered. Based on the teachings herein, the skilled artisan can readily adjust the parameters of the phototransfection process to control the approximate number of nucleic molecules that enter the neuron per pulse.

In one embodiment, a cell is surrounded by an nucleic acid bath comprising a nucleic acid molecule, preferably an RNA molecule, at about 1 to about 150 µg/ml, more preferably about 10 to about 100 µg/ml, and more preferably still at about 10 to about 50 µg/ml in the bath, Preferably the bath is in a container that is permeable by a laser and does not distort the beam, even more preferably, the bath is optically clear glass with a thickness of about 0.1 mm.

In another embodiment, a cell is bathed in discrete locations on the cell surface with a solution comprising a nucleic acid molecule. For instance, using a patch pipette, micropipette or other applicator, a solution comprising nucleic acid is applied to a discrete location on the surface of a cell. The solution may be applied to more than one location on a cell. The cell is then irradiated using a laser at one or more sites within a discrete location. Nucleic acid in the solution is present at about 1 nanogram per microliter (ng/µl) to about 2 microgram/microliter (µg/µl), preferably about 50 ng/µl to about 1 µg/µl, and more preferably about 100 ng/µl to about 500 ng/µl.

The present invention further comprises the use of other methods for introducing a nucleic acid to a cell, tissue or animal via phototransfection. Methods included in the present invention include, for example, perfusion, picospritzing, microinjection and the like. Methods for perfusion include, but are not limited to, using a pump to move a fluid medium comprising a nucleic acid, preferably RNA, even more preferably mRNA, to a cell, tissue or animal. The fluid medium used in the perfusion methods of the present invention can included those disclosed elsewhere herein, such as buffered solutions that support and maintain the stability of a nucleic acid and a cell, tissue or animal. In one embodiment of the present invention, the fluid medium can include a medium, such as Basal Media Eagle (BME), BGJb Medium, Brinster's BMOC-3 Medium, CMRL Medium, $CO_2$-Independent Medium, Dulbecco's Modified Eagle Media (D-MEM), F-10 Nutrient Mixtures, F-12 Nutrient Mixtures, Glasgow Minimum Essential Media, Grace's Insect Cell Culture Media, Improved MEM, IPL-41 Insect Media, Iscove's Modified Dulbecco's Media, Leibovitz's L-15 Media, McCoy's 5A Media (modified), MCDB 131 Medium, Media 199, Medium NCTC-109, Minimum Essential Media (MEM), Modified Eagle Medium (MEM), Opti-MEM® I Reduced Serum Media, RPMI Media 1640, Schneider's Drosophila Medium, Waymouth's MB 752/1 Media, Williams Media E, artificial spinal fluid (aCSF), Ringer's solution and the like. The present invention can further comprise the use of buffered salt solutions, including, but not limited to, Dulbecco's Phosphate-Buffered Saline (D-PBS), Earle's Balanced Salt Solution, Hanks' Balanced Salt Solution, Phosphate-Buffered Saline (PBS), and the like.

The present invention further comprises using picospritzing in conjunction with phototransfection to introduce a nucleic acid to a cell, organ or tissue. Picospritzing comprises the use of electrical pulses with a pressure device to deliver a compound, such as a nucleic acid, to a cell, tissue or animal. Method for picospritzing are known in the art and are described in, for example, Herberholz, et al., 2002, J. Neuroscience, 22: 9078-9085). Picospritzing apparatuses are available from, for example, World Precision Instruments (Sarasota, Fla.).

In another embodiment, transfection of cells with nucleic acids encoding two or more different polypeptides is effected by microinjection. In these embodiments, the recipient cell is preferably a somatic cell, preferably a somatic, differentiated cell.

The present invention comprises irradiating a cell with a laser to phototransfect and locally transfect the cell. When the laser contacts the cell membrane, or cell wall in the case of plant cells, fungal cells, and other cells comprising a cell wall, the plasma membrane or cell wall is perforated, permitting the diffusion of foreign molecule, such as RNA and/or DNA, to enter the cell. The fluidity of mammalian cell membranes facilitates subsequent closure of the perforation. Lasers compatible with the present invention include, but are not limited to, continuous-wave argon-ion lasers operating at 488 nm (Schneckenburger, et al., 2002, J. Biomed. Opt., 7: 410-416; Palumbo et al., 1996, J. Photochem. Photobiol. B-Biol., 36: 41-46), pulsed and frequency upconverted Nd:YAG lasers operating at 355 nm (Shirahata, et al., 2001, J. Invest. Med., 49; 184-190), 532 nm (Soughayer, et al., 2000, Anal. Chem., 72; 1342-1347), and 1064 nm (Mohanty, et al., 2003, Biotechnol. Lett. 25: 895-899), and femtosecond titanium-sapphire lasers (Tirlapur, et al., 2002, Plant J. 31: 365-374; Tirlapur, et al., 2002, Nature 418: 290-291; Zeira, et al., 2003, Mol. Therapy 8: 342-350). Preferably, a titanium-sapphire laser at 405 nm (PicoQuant GmbH, Berlin Germany) is used to phototransfect a cell. However, the present invention is not limited to the a titanium-sapphire laser, but includes any laser with the capacity of delivering a localized focal volume of about $10^{-19}$ $m^3$.

Control of the incident laser beam is achieved by using various apparatuses to control the focus and power of the laser, as well as to aim the laser. Focusing the laser is achieved by passing the incident laser through a lens, such as a microscope lens, placed between the laser and the cell. The power of the laser in controlled by modulating the voltage and current going to the laser and through the use of neutral density filters or pockels cells. Exposure of the cells to the laser is controlled through a shutter, such as a single lens reflex (SLR) camera shutter and/or with electronically controlled pockels cells.

Aiming the laser is accomplished through a microscope lens and with dielectric and steering mirrors and AOD (acoustic optical deflector) between the laser source and a cell. A microscope useful in the practice of the present invention includes, but is not limited to, a confocal microscope, a multiphoton excitation fluorescence microscope, a light microscope, and the like. The present method further comprises aiming the laser using an optical fiber to transmit the laser to a distant or difficult-to-access area. As a non-limiting example, an optical fiber is used to phototransfect intestinal, neural or cardiothoracic cells in a live animal. Further, the present invention comprises phototransfecting a cell or a population of cells using multiple optical fibers in an animal. Optical fibers are well known in the art and are described in, for example, U.S. Pat. Nos. 3,711,262 6,973, 245.

A laser beam with less than a milliwatt of power for tens of milliseconds is sufficient to porate a cell (Paterson, et al., 2005, Optics Express, 13: 595-600). Preferably, the laser has a power density of about 1200 $MWm^{-2}$ and a total power of about 30-55 mW at the back aperture of the lens. Further, in order to provide maximum surface area for transfection; the laser beam should be highly circular (dx=dy) with beam diameter of about 2 mm.

The starting power output of the laser is attenuated through the use of various filters, such as a neutral density (ND) filter to reduce the power to the milliwatt range required for phototransfection with no attendant pathological effects on the target cell. The beam can be expanded through the used of a telescope where f=100 mm, and directed into a microscope, such as a light microscope or an oil-immersion microscope with a ×100 objective (N.A.=1.25). An SLR shutter between the laser source and the microscope permits control of the exposure time. An exposure time of about 40 ms is sufficient to porate a cell without attendant damage, but this parameter can be altered to increase or decrease exposure time.

Target cells in a nucleic acid bath are positioned and focused on by manipulating the stage of the microscope and/or using dielectric and steering mirrors and AOD, so the beam is focused on the cell membrane and not towards the nucleus of the cell. When porating a cellular process, such as a dendrite, the beam is focused directly on the cellular process.

The cell or cellular process is irradiated with a laser according to the parameters disclosed herein. In one embodiment, the cells are transfected with a nucleic acid comprising a marker that indicates a successful transfection. Such markers are known in the art and include, for example, antibiotic resistance and fluorescent proteins. Successful poration can be tracked by the addition of a detectable molecule to the nucleic acid solution. Such molecules are well known in the art. Preferably, the molecule is non-toxic to the recipient cell. Non-limiting examples include Lucifer yellow and carboxyfluorescein diacetate succinimidyl ester. The cells are incubated according to the incubation conditions prior to irradiation with the laser. Expression of the locally transfected nucleic acid is analyzed according to the presence and activity of a marker or the phenotype of the cell.

Kits

The present invention encompasses various kits which comprise a compound, including a nucleic acid, for use in the phototransfection methods of the present application. The kits of the present invention can further comprise an applicator, and instructional materials which describe use of a nucleic acid to perform the methods of the invention. Although model kits are described below, the contents of other useful kits will be apparent to the skilled artisan in light of the present disclosure. Each of these kits is contemplated within the present invention.

In one aspect, the invention includes a kit for phototransfecting a cell, tissue, such as a live slice, or an animal, preferably a mammal. The kit comprises a container comprising a nucleic acid, preferably mRNA, that when expressed confers a specific phentotype on the phototransfected cell, tissue or animal. That is, the kit of the present invention comprises a mixture of mRNA or nucleic acids derived from mRNA as described elsewhere herein that confers a specific phenotype to a cell. Such phenotypes include those disclosed elsewhere herein, such as a cancerous phenotype, the phenotype from a specific developmental stage, the phenotype from a specific stage induced by the administration of a drug, and the like. As an example, the mRNA isolated from a stem cell can be encompassed in the kit of the present invention, and can then be phototransfected into a cell to confer a stem cell phenotype on the phototransfected cell. As another example, the mRNA from non-cancerous cell can be phototransfected into a cancerous cell to confer a non-cancerous phenotype on that cell.

In another embodiment, a kit comprises a container comprising a mixture of RNAs in essentially the same relative abundance as found in a particular cell in a particular physiological state, wherein the RNAs are capable of phenotypically converting a cell when introduced therein. In yet another, a kit comprises a container comprising a mixture of nucleic acid wherein the mixture is phenotype-converting. In another embodiment, the kit comprises a container comprising a Mixture of RNA comprising two or more RNAs encoding two or more different polypeptides and where the two or more RNAs are in the same relative abundance as is found in a cell. The RNA in any of the kits of the invention can be obtained by mRNA isolation, chemical synthesis and/or in vitro transcription. The present examples are not limited to cells however, and can also include mRNA from an tissue, such as a live slice, or an animal, preferably a mammal. Additionally, the kit comprises an applicator and an instructional material for the use of the kit. These instructions simply embody the disclosure provided herein.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Experimental Example 1

Neurons Phototransfected with mRNA from Astrocytes

The materials and methods used in the experiment presented in the Experimental Example below are now described.

Recipient cell preparation: Rat hippocampal neurons were cultured under standard culture conditions on gridded coverslips. The neurons were treated with α-amanitin at 100 ng/ml and TSA at 100 nM for 48 hours before phototransfection. The coverslips with inhibitor-treated recipient cells were then incubated in normal hippocampal solution (NHS) containing 100 ng/ml of α-amanitin, 5 antibiotics (Penicillin-Streptomycin, Gentamicin, Neomycin and Kanamycin) and FUNGIZONE (amphotericin B; E.R. Squibb & Sons, Princeton, N.J.) during the phototransfection procedure.

Donor mRNA preparation: Rat astrocytes cultured in DMEM/10% FBS in a flask using standard protocol. The flask was shaken overnight to ensure the purity of asctrocyte population. Total RNA was then extracted using TRIZOL and according to manufacturer's recommendations, followed by mRNA extraction using MICRO-FASTTRACK 2.0 kit. mRNA was dissolved in a elution buffer (10 mM Tris-Cl in DEPC water) at a final concentration of 100 ng/ul to about 300 ng/ul and frozen at −80° C. for future use as donor mRNA.

Phototransfection: Recipient cells in NHS (supplemented with α-amanitin, antibiotics & FUNGIZONE) were imaged under a 40× water immersed lens and scanned by the Chameleon laser. The area to be transfected on each cell was outlined on an image of the cell on the monitor. A local application of about 100~300 ng/□l mRNA from rat astrocytes directly onto the cell body using a micropipette and 16 (4×4) points within the outlined area were porated sequentially using a Ti-sapphire laser (Mai-Tai™, Newport Corporation, Spectra-Physics Laser division, Mountain View, Calif.) for 5 milliseconds per point at 35 mW laser power (at the back aperture of the lens). About 0.5 to about 1 microliter of mRNA solution was applied to each neuron. The mRNA solution also contained Lucifer yellow to track the correct aspiration of the mRNA solution sprayed onto the cell to be transfected.

Post phototransfection: After phototransfection with donor mRNA, the recipient cells were incubated in recipient-cell-specific medium with 25 ng/ml α-amanitin (as well as antibiotics and FUNGIZONE as before) for 6 hours before replacing with regular recipient-cell-specific medium containing antibiotics and FUNGIZONE but without α-amanitin. Thereafter, the phototransfected cells on coverslips were cultured in the appropriate donor cell specific media post withdrawal of α-amanitin. Culture media was subsequently changed twice per week.

Imaging and Staining: Recipient cells were imaged prior to phototransfection and periodically after phototransfection. Cells were stained with 4',6-diamidino-2-phenylindole (DAPI) to detect the nuclei. Differential interference contrast (DIC) images were taken to assess morphology of the phototransfected cells. For immunohistochemical detection of glial fibrially acidic protein (GFAP), cells were fixed by exposure to 4% paraformaldehyde for 10 minutes. The sample was then incubated with mouse antibody (1:400) against glial fibrillary acidic protein (GFAP) overnight at 4° C., followed by incubation with a fluorophore-conjugated goat anti-mouse antibody (1:1500) for 45 minutes at room temperature.

Physiology (Calcium imaging): Phototransfected cells were loaded with with a cell-permeant fluorescent calcium indicator (fluo-4 AM) and imaged by confocal microscopy. First, cells were stimulated with 100 μM glutamate. Cells were then washed and allowed to recovery (signal returning to baseline). Cells were then stimulated with 50 mM potassium. Cells were washed again and monitored to evaluate if signal returned to baseline.

The results of the experiments are now described and discussed.

Two weeks after phototransfection of astrocyte mRNA into hippocampal neuron cells, morphological changes were clearly evident. In particular, the retraction of neuronal processes in phototransfected cells was observed. See FIGS. 3A, 3B and 3C.

Figure 4A:
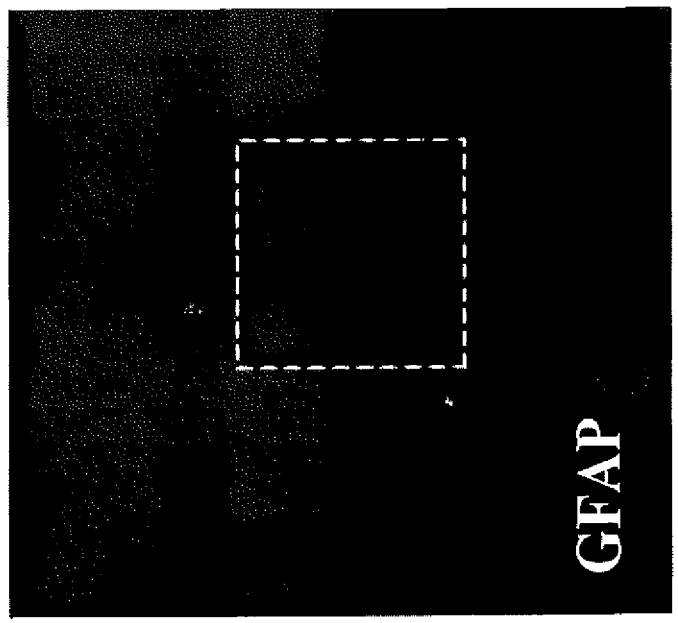
FIGS. 4A and 4B are images of a representative rat hippocampal neuron cell before and 3 weeks after phototransfection.
Figure 4B:
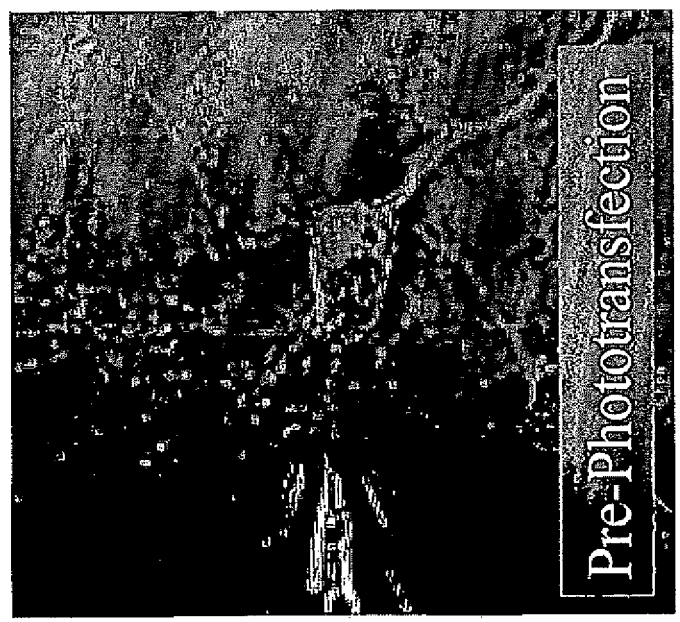
Figure 5B:
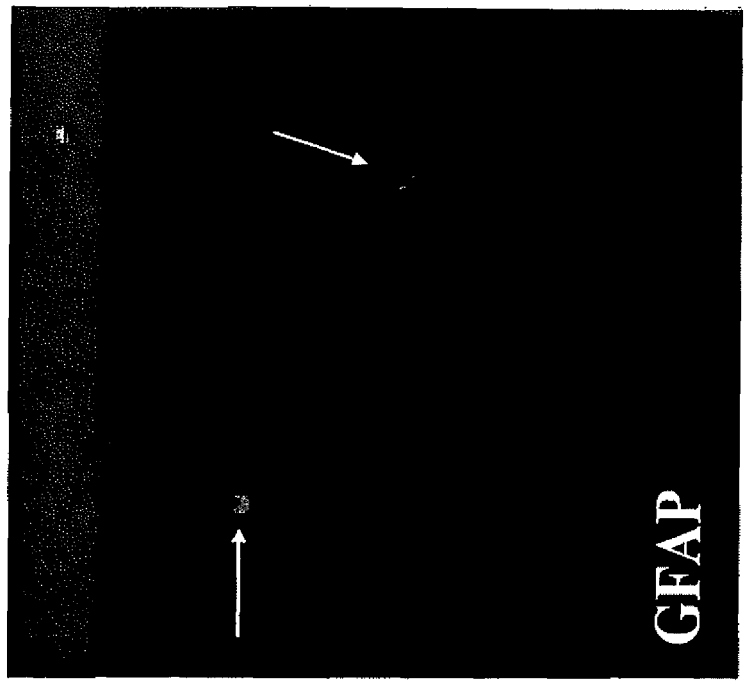
FIGS. 5A and 5B are images of two representative phototransfected rat hippocampal neuron cells 8 weeks after phototransfection with rat astrocyte mRNA.
Figure 5A:
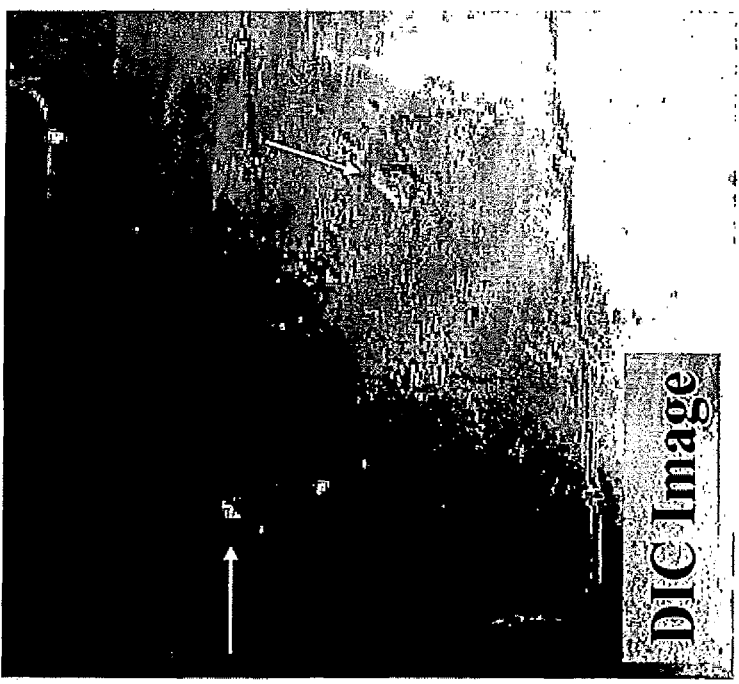

In addition, immunohistochemical staining for glial fibrillary acidic protein (GFAP) was performed. GFAP is protein specifically expressed in glial cells; it is not expressed in hippocampal neurons. The in vivo half-life of GFAP mRNA is about 5 hours and the in vivo half-life of GFAP protein is about 18 hours. Therefore, two weeks after phototransfection, glial-cell derived GFAP mRNA and any GFAP protein expressed from it would not be expected to present in the phototransfected cell. Remarkably, GFAP was detected on phototransfected cells (FIG. 3D). GFAP was also detected at both 3 weeks (FIGS. 4A and 4B) and 8 weeks (FIGS. 5A and 5B) after phototransfection of glial mRNA into hippocampal neurons. Retraction of neuronal processes was also maintained at 8 weeks post-phototransfection (FIG. 5A). These data indicate, therefore, that the endogenous GFAP gene in the phototransfected neuron cell was being expressed. This data thus suggests that phototransfection of total glial mRNA results in the activation of long-term expression of genes underlying glial cell phenotype. These indicators of phenotype conversion persisted in phototransfected cells for over 3 months.

Calcium imaging experiments were performed to assess calcium uptake as a function of glutamate stimulation and potassium stimulation. Both astrocytes and neurons have glutamate receptors. Activation of the glutamate receptors by the presence of glutamate leads to an increase in cytosolic calcium. However, only neurons have voltage-gated calcium channels (i.e., electrical excitability). When the membrane potential of a neuron is properly hyperpolarized by electrical stimulation or high potassium concentration, calcium influx to the cytosol results. This difference in calcium uptake, therefore, can be used to physiologically distinguish between astroglial cells and neuron cells.

Figures 6A, 6B, 6C, 6D, 6E:
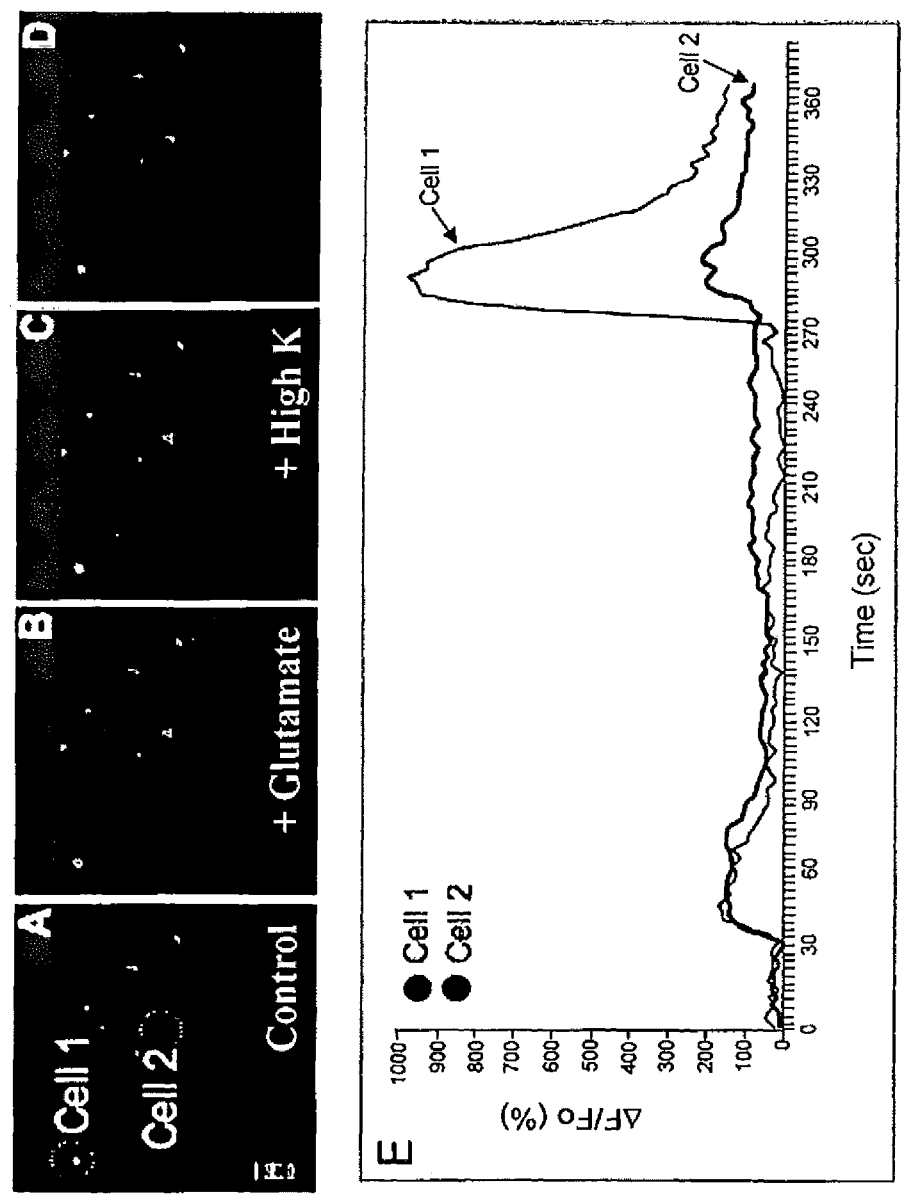
FIGS. 6A to 6E is a series of representative confocal microscopy images of neuronal cells and a graph of calcium imaging data for two of the cells. Images were captured every 3 seconds.

FIG. 6A shows two cells loaded with a fluorescent calcium indicator at 3 weeks after phototransfection, and is a representative image of the baseline signal for the two cells. Cell 1 is a control cell. Cell 2 was transfected with astrocyte mRNA. Stimulation of the cells with glutamate resulted in calcium uptake in both cells (FIG. 6B). The increase in the graph in FIG. 6E at about 35 seconds is the response to the glumate stimulation. FIG. 6B is a representative image of the cells during the glutamate-induced increase. After washing the cells and allowing them to recover, stimulation with high potassium induced a rapid and maximal spike (starting at about 270 seconds) of calcium uptake in Cell 1. High potassium stimulation resulted in a delayed and limited calcium increase in Cell 2. See FIGS. 6C and 6E. After the potassium was washed away, both cells returned to baseline signal (FIG. 6D), indicating that the stimulations were not toxic to the cells.

The spike of calcium uptake observed in Cell 1 is expected if a cell has a neuronal phenotype. The result in Cell 2 is in notable contrast. The delayed and limited calcium uptake in Cell 2 indicates the reduction in number or absence of voltage-gated calcium channels. Thus, these data demonstrate that transfected cells possess intact, functional glutamate receptors (FIG. 6B) however, an important feature of neuronal phenotype has changed in Cell 2: the loss of voltage-gated calcium channels (FIGS. 6C and 6E).

These data indicate that a multigenic phenotype in a first cell type can be induced in a second cell type by phototransfecting mRNA from the first cell into the second cell in accordance with the invention. The phenotype conversion is stable for months, which indicates that the gene expression profile in the recipient cell is stably converted to the expression profile of the mRNA donor cell and is maintained.

Experimental Example 2

Neurons Phototransfected with mRNA from Neonatal Cardiomyocytes

Rat hippocampal neurons were prepared as recipient cells as described in Experimental Example 1. mRNA was obtained from rat neonatal cardiomyocytes essentially as described above. Neurons were phototransfected as described in Experimental Example 1. Six (6) hours after phototransfection, the phototransfected neurons were removed from neual basal/B27 medium to DMEM/10% FBS, a medium suitable for culture of cardiomyocytes. Seven (7) days post-phototransfection, the phototransfected neurons were transferred to DMED/10% FBS/G5 supplement medium.

Experimental Example 3

Fibroblasts Phototransfected with mRNA from Nestin-Positive ES Cells

Mouse fibroblasts were prepared as recipient cells essentially as described in Experimental Example 1. mRNA was prepared from mouse nestin-positive embryonic stem cells essentially as described in Experimental Example 1. Fibroblasts were phototransfected as described in Experimental Example 1, however, 64 (8×8) points were porated at 55 mW each. Twenty-four (24) hours after phototransfection, the phototransfected fibroblasts were moved from DMEM (without sodium pyruvate)/10% FBS medium into DMEM/F12/N2 supplement/ascorbic acid medium, which is suitable for culturing ES cells.

Experimental Example 4

Fibroblasts Phototransfected with mRNA from Astrocytes

Mouse fibroblasts were prepared as recipient cells essentially as described in Experimental Example 1. mRNA was prepared from mouse astrocytes essentially as described in Experimental Example 1. Fibroblasts were phototransfected as described in Experimental Example 1, however, 64 (8×8) points were porated at 55 mW each. Six (6) hours after phototransfection, the phototransfected fibroblasts were moved from DMEM (without sodium pyruvate)/10% FBS medium into DMEM/10% FBS medium.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of transferring a phenotype of a donor cell to a recipient cell, the method comprising:
    transfecting a recipient cell with a transcriptome of a donor cell a first time, wherein the cell type of the donor cell is different than the cell type of the recipient cell, wherein the recipient cell is transfected in vitro or ex vivo, wherein the RNAs of the transcriptome enter the recipient cell, wherein the RNAs are functional in the recipient cell, and
    transfecting the recipient cell with a transcriptome of the donor cell at least a second time, wherein the recipient cell is transfected in vitro or ex vivo, wherein the RNAs of the transcriptome enter the recipient cell, wherein the RNAs are functional in the recipient cell,
    thereby initiating a change in physiology and morphology of the recipient cell, wherein the change in physiology and morphology yields a phenotype of the recipient cell that is indicative of the donor cell
    wherein the donor cell and recipient cell are selected from the group consisting of:
    a) wherein the recipient cell is a fibroblast, and wherein the donor cell is selected from the group consisting of an astrocyte, a cardiomyocyte, and a stem cell;
    b) wherein the recipient cell is a neuron, and wherein the donor cell is selected from the group consisting of an astrocyte and a cardiomyocyte; and
    c) wherein the recipient cell is an astrocyte and wherein the donor cell is a cardiomyocyte.

2. The method of claim 1, wherein the method further comprises transfecting the recipient cell with at least one DNA of the donor cell.

3. The method of claim 1, wherein the RNA is at least one selected from the group consisting of: mRNA, siRNA, miRNA, hnRNA, and tRNA.

4. The method of claim 1, wherein the RNAs are expressed by the recipient cell.

5. The method of claim 1, wherein the RNAs are isolated from a donor cell.

6. The method of claim 1, wherein RNAs are in vitro transcribed.

7. The method of claim 1, wherein the RNAs are prepared by a method selected from the group consisting of: mRNA isolation from a donor cell, in vitro mRNA transcription or mRNA chemical synthesis.

8. The method of claim 1, wherein the phenotype of the recipient cell comprises two or more characteristics selected from the group consisting of: expression of the donor cell nucleic acid, protein expression of donor cell protein, expression of donor cell immunological markers, donor cell morphology, donor cell physiology, donor cell bioproduct synthesis, and donor cell membrane lipid composition.

9. The method of claim 1, wherein the phenotype-of the recipient cell comprises three or more phenotype characteristics selected from the group consisting of: expression of the donor cell nucleic acid, protein expression of donor cell protein, expression of donor cell immunological markers, donor cell morphology, donor cell physiology, donor cell bioproduct synthesis, and donor cell membrane lipid composition.

10. The method of claim 1, wherein the phenotype-of the recipient cell comprises four or more phenotype characteristics selected from the group consisting of: expression of the donor cell nucleic acid, protein expression of donor cell protein, expression of donor cell immunological markers, donor cell morphology, donor cell physiology, donor cell bioproduct synthesis, and donor cell membrane lipid composition.

11. The method of claim 1, wherein the phenotype-of the recipient cell comprises the phenotype characteristics of donor cell morphology and donor cell physiology.

12. The method of claim 1, wherein the recipient cell is a fibroblast, and wherein the donor cell is selected from the group consisting of an astrocyte, a cardiomyocyte, and a stem cell.

13. The method of claim 1, wherein the recipient cell is a neuron, and wherein the donor cell is selected from the group consisting of an astrocyte and a cardiomyocyte.

14. The method of claim 1, wherein the recipient cell is an astrocyte and wherein the donor cell is a cardiomyocyte.

* * * * *